(12) United States Patent
LeCloux et al.

(10) Patent No.: US 8,759,818 B2
(45) Date of Patent: Jun. 24, 2014

(54) DEUTERATED COMPOUNDS FOR ELECTRONIC APPLICATIONS

(75) Inventors: Daniel David LeCloux, Wilmington, DE (US); Adam Fennimore, Wilmington, DE (US); Weiying Gao, Landenberg, PA (US); Nora Sabina Radu, Landenberg, PA (US); Weishi Wu, Landenberg, PA (US); Vsevolod Rostovtsev, Swarthmore, PA (US); Michael Henry Howard, Jr., Montchanin, DE (US); Hong Meng, Wilmington, DE (US); Yulong Shen, Wilmington, DE (US); Jeffrey A. Merlo, Wilmington, DE (US); Eric Maurice Smith, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 218 days.

(21) Appl. No.: 12/643,420

(22) Filed: Dec. 21, 2009

(65) Prior Publication Data
US 2011/0037057 A1 Feb. 17, 2011

Related U.S. Application Data

(60) Provisional application No. 61/239,574, filed on Sep. 3, 2009.

(51) Int. Cl.
*H01L 29/08* (2006.01)
*H01L 51/00* (2006.01)
*C07B 59/00* (2006.01)
*C07D 307/87* (2006.01)
*C07C 15/28* (2006.01)
*C07D 209/86* (2006.01)
*C07D 307/91* (2006.01)
*H01L 51/50* (2006.01)

(52) U.S. Cl.
CPC .......... *H01L 51/0058* (2013.01); *C07B 59/001* (2013.01); *C07D 307/87* (2013.01); *C07B 2200/05* (2013.01); *C07C 15/28* (2013.01); *H01L 51/0052* (2013.01); *C07D 209/86* (2013.01); *C07D 307/91* (2013.01); *C07C 2103/24* (2013.01); *H01L 51/5036* (2013.01); *H01L 51/006* (2013.01)
USPC .......... 257/40; 257/E51.05; 313/504; 546/255

(58) Field of Classification Search
USPC .............................................. 257/40, E51.05
See application file for complete search history.

(56) References Cited

U.S. PATENT DOCUMENTS 3,282,875 A 11/1966 Connolly et al.
3,849,458 A 11/1974 Dinh-Nguyen
(Continued)

FOREIGN PATENT DOCUMENTS

CN 1416301 A 5/2003
CN 1668719 A 9/2005
(Continued)

OTHER PUBLICATIONS

CRC Handbook of Chemistry and Physics, 81st Edition (2000-2001) (Book Not Included).
(Continued)

*Primary Examiner* — Amar Movva

(57) ABSTRACT

This invention relates to deuterated aryl-anthracene compounds that are useful in electronic applications. It also relates to electronic devices in which the active layer includes such a deuterated compound.

28 Claims, 4 Drawing Sheets

(56) References Cited

U.S. PATENT DOCUMENTS

| | | |
|---|---|---|
| 4,053,311 A | 10/1977 | Limburg et al. |
| 4,358,545 A | 11/1982 | Ezzell et al. |
| 4,940,525 A | 7/1990 | Ezzell |
| 5,247,190 A | 9/1993 | Friend et al. |
| 5,254,633 A | 10/1993 | Han |
| 5,378,519 A | 1/1995 | Kikuchi et al. |
| 5,408,109 A | 4/1995 | Heeger et al. |
| 5,707,747 A | 1/1998 | Tomiyama et al. |
| 5,911,918 A | 6/1999 | Shacklette et al. |
| 5,929,194 A | 7/1999 | Woo et al. |
| 5,936,259 A | 8/1999 | Katz et al. |
| 5,962,631 A | 10/1999 | Woo et al. |
| 6,150,426 A | 11/2000 | Curtin et al. |
| 6,259,202 B1 | 7/2001 | Sturm et al. |
| 6,303,238 B1 | 10/2001 | Thompson et al. |
| 6,579,630 B2 | 6/2003 | Li et al. |
| 6,670,645 B2 | 12/2003 | Grushin et al. |
| 6,677,060 B2 | 1/2004 | Li et al. |
| 6,686,067 B2 | 2/2004 | Li et al. |
| 6,852,429 B1 | 2/2005 | Li et al. |
| 6,872,475 B2 | 3/2005 | Chen et al. |
| 6,875,524 B2 | 4/2005 | Hatwar et al. |
| 6,902,833 B2 | 6/2005 | Thompson et al. |
| 6,953,705 B2 | 10/2005 | Prakash |
| 7,023,013 B2 | 4/2006 | Ricks et al. |
| 7,075,102 B2 | 7/2006 | Grushin et al. |
| 7,125,952 B2 | 10/2006 | O'Dell et al. |
| 7,129,386 B2 | 10/2006 | Saitoh et al. |
| 7,173,131 B2 | 2/2007 | Saitoh et al. |
| 7,189,989 B2 | 3/2007 | Ise |
| 7,211,202 B2 | 5/2007 | Korzhenko et al. |
| 7,235,420 B2 | 6/2007 | Prakash et al. |
| 7,351,358 B2 | 4/2008 | Hsu et al. |
| 7,358,409 B2 | 4/2008 | Saitoh et al. |
| 7,362,796 B2 | 4/2008 | Shigeno |
| 7,365,230 B2 | 4/2008 | Herron et al. |
| 7,375,250 B2 | 5/2008 | Saitoh et al. |
| 7,390,438 B2 | 6/2008 | Hsu et al. |
| 7,402,681 B2 | 7/2008 | Ong et al. |
| 7,431,866 B2 | 10/2008 | Hsu et al. |
| 7,456,424 B2 | 11/2008 | Wu et al. |
| 7,462,298 B2 | 12/2008 | Hsu et al. |
| 7,491,450 B2 | 2/2009 | Okinaka et al. |
| 7,528,542 B2 | 5/2009 | Kawamura et al. |
| 7,540,978 B2 | 6/2009 | Pfeiffer et al. |
| 7,586,006 B2 | 9/2009 | Funahashi |
| 7,642,380 B2 | 1/2010 | Funahashi |
| 7,651,786 B2 | 1/2010 | Matsuura et al. |
| 7,651,788 B2 | 1/2010 | Seo et al. |
| 7,709,104 B2 | 5/2010 | Saitoh et al. |
| 7,722,785 B2 | 5/2010 | Hsu et al. |
| 7,745,017 B2 | 6/2010 | Nakamura et al. |
| 7,887,933 B2 | 2/2011 | Kathirgamanathan et al. |
| 8,012,609 B2 | 9/2011 | Takeda |
| 8,026,665 B2 | 9/2011 | Kim et al. |
| 8,063,399 B2 | 11/2011 | Johansson et al. |
| 8,137,823 B2 | 3/2012 | Kim et al. |
| 8,343,381 B1 | 1/2013 | Chesterfield |
| 2001/0026878 A1 | 10/2001 | Woo et al. |
| 2001/0053462 A1 | 12/2001 | Mishima |
| 2002/0048687 A1 | 4/2002 | Hosokawa et al. |
| 2002/0076576 A1 | 6/2002 | Li et al. |
| 2002/0155319 A1 | 10/2002 | Kawamura et al. |
| 2003/0072966 A1 | 4/2003 | Hosokawa et al. |
| 2003/0118866 A1 | 6/2003 | Oh et al. |
| 2003/0134140 A1 | 7/2003 | Li |
| 2003/0138657 A1 | 7/2003 | Li |
| 2003/0168970 A1 | 9/2003 | Tominaga et al. |
| 2003/0224205 A1 | 12/2003 | Li et al. |
| 2003/0227001 A1 | 12/2003 | Li et al. |
| 2004/0004433 A1 | 1/2004 | Lamansky et al. |
| 2004/0038459 A1 | 2/2004 | Brown et al. |
| 2004/0082250 A1 | 4/2004 | Haoto |
| 2004/0094768 A1 | 5/2004 | Yu et al. |
| 2004/0102577 A1 | 5/2004 | Hsu et al. |
| 2004/0106003 A1 | 6/2004 | Chen et al. |
| 2004/0106004 A1 | 6/2004 | Li |
| 2004/0121184 A1 | 6/2004 | Thompson et al. |
| 2004/0127637 A1 | 7/2004 | Hsu et al. |
| 2004/0209118 A1 | 10/2004 | Seo et al. |
| 2004/0263067 A1 | 12/2004 | Saitoh et al. |
| 2005/0031898 A1 | 2/2005 | Li et al. |
| 2005/0035335 A1 | 2/2005 | Han et al. |
| 2005/0063638 A1 | 3/2005 | Alger et al. |
| 2005/0064233 A1 | 3/2005 | Matsuura et al. |
| 2005/0073249 A1 | 4/2005 | Morii et al. |
| 2005/0074630 A1 | 4/2005 | Kanno et al. |
| 2005/0106415 A1 | 5/2005 | Jarikov et al. |
| 2005/0158577 A1 | 7/2005 | Ishibashi et al. |
| 2005/0184287 A1 | 8/2005 | Herron et al. |
| 2005/0186106 A1 | 8/2005 | Li et al. |
| 2005/0187411 A1 | 8/2005 | Herron et al. |
| 2005/0191776 A1 | 9/2005 | Lamansky et al. |
| 2005/0205860 A1 | 9/2005 | Hsu et al. |
| 2005/0244670 A1 | 11/2005 | Saitoh et al. |
| 2005/0245752 A1 | 11/2005 | Conley et al. |
| 2005/0280008 A1* | 12/2005 | Ricks et al. ............... 257/79 |
| 2006/0033421 A1 | 2/2006 | Matsuura et al. |
| 2006/0043858 A1 | 3/2006 | Ikeda et al. |
| 2006/0052641 A1 | 3/2006 | Funahashi |
| 2006/0076557 A1 | 4/2006 | Waller et al. |
| 2006/0099447 A1 | 5/2006 | Lee et al. |
| 2006/0103298 A1 | 5/2006 | Lee |
| 2006/0113528 A1 | 6/2006 | Okinaka et al. |
| 2006/0115676 A1 | 6/2006 | Igawa et al. |
| 2006/0115678 A1 | 6/2006 | Saitoh et al. |
| 2006/0121312 A1 | 6/2006 | Yamada et al. |
| 2006/0127698 A1 | 6/2006 | Tokailin et al. |
| 2006/0128969 A1 | 6/2006 | Li et al. |
| 2006/0134459 A1 | 6/2006 | Huo |
| 2006/0152146 A1 | 7/2006 | Funahashi |
| 2006/0154107 A1 | 7/2006 | Kubota et al. |
| 2006/0158102 A1 | 7/2006 | Kawamura et al. |
| 2006/0159838 A1 | 7/2006 | Kowalski et al. |
| 2006/0194074 A1 | 8/2006 | Funahashi |
| 2006/0210830 A1 | 9/2006 | Funahashi |
| 2006/0216411 A1 | 9/2006 | Steudel et al. |
| 2006/0216633 A1 | 9/2006 | Kubota et al. |
| 2006/0217572 A1 | 9/2006 | Kawamura et al. |
| 2006/0251925 A1 | 11/2006 | Hosokawa et al. |
| 2006/0267488 A1 | 11/2006 | Saitoh et al. |
| 2006/0284140 A1 | 12/2006 | Breuning et al. |
| 2007/0031588 A1 | 2/2007 | Nakayama |
| 2007/0031701 A1 | 2/2007 | Nakashima et al. |
| 2007/0032632 A1 | 2/2007 | Tsukioka et al. |
| 2007/0063638 A1 | 3/2007 | Tokairin et al. |
| 2007/0066755 A1 | 3/2007 | Hsu et al. |
| 2007/0079927 A1 | 4/2007 | Lamansky et al. |
| 2007/0096082 A1 | 5/2007 | Gaynor et al. |
| 2007/0099024 A1 | 5/2007 | Nii et al. |
| 2007/0114917 A1 | 5/2007 | Funahashi et al. |
| 2007/0134511 A1 | 6/2007 | Kawamura et al. |
| 2007/0155991 A1 | 7/2007 | Funahashi |
| 2007/0181874 A1 | 8/2007 | Prakash et al. |
| 2007/0182321 A1 | 8/2007 | Kinoshita et al. |
| 2007/0189190 A1 | 8/2007 | Feng et al. |
| 2007/0205409 A1 | 9/2007 | Lecloux et al. |
| 2007/0215864 A1 | 9/2007 | Luebben et al. |
| 2007/0228364 A1 | 10/2007 | Radu et al. |
| 2007/0236137 A1 | 10/2007 | Funahashi |
| 2007/0247063 A1 | 10/2007 | Murase et al. |
| 2007/0252511 A1 | 11/2007 | Funahashi |
| 2007/0255076 A1 | 11/2007 | Ito et al. |
| 2007/0257609 A1 | 11/2007 | Fukuda |
| 2007/0285009 A1 | 12/2007 | Kubota |
| 2007/0292713 A9 | 12/2007 | Dobbs et al. |
| 2007/0298530 A1 | 12/2007 | Feehery |
| 2008/0023676 A1 | 1/2008 | Hsu |
| 2008/0049413 A1 | 2/2008 | Jinde et al. |
| 2008/0067473 A1 | 3/2008 | Walker et al. |
| 2008/0071049 A1 | 3/2008 | Radu et al. |
| 2008/0086012 A1 | 4/2008 | Egawa et al. |
| 2008/0097076 A1 | 4/2008 | Radu et al. |
| 2008/0102312 A1 | 5/2008 | Parham et al. |

(56) References Cited

U.S. PATENT DOCUMENTS

| | | | |
|---|---|---|---|
| 2008/0114178 A1 | 5/2008 | Kawakami et al. |
| 2008/0138655 A1 | 6/2008 | Lecloux et al. |
| 2008/0166566 A1 | 7/2008 | Prakash |
| 2008/0191614 A1 | 8/2008 | Kim et al. |
| 2008/0233433 A1 | 9/2008 | Tatsuya et al. |
| 2008/0286566 A1 | 11/2008 | Prakash |
| 2008/0286605 A1 | 11/2008 | Akira |
| 2008/0297037 A1* | 12/2008 | Vestweber et al. ............ 313/504 |
| 2008/0303425 A1 | 12/2008 | Rostovtsev et al. |
| 2008/0303427 A1 | 12/2008 | Johansson et al. |
| 2008/0303428 A1 | 12/2008 | Rostovtsev et al. |
| 2008/0315753 A1 | 12/2008 | Liao et al. |
| 2008/0315754 A1 | 12/2008 | Kawamura et al. |
| 2009/0051281 A1 | 2/2009 | Inoue |
| 2009/0058279 A1 | 3/2009 | Akira |
| 2009/0079334 A1 | 3/2009 | Kim et al. |
| 2009/0114909 A1 | 5/2009 | Li et al. |
| 2009/0134781 A1 | 5/2009 | Jang et al. |
| 2009/0184635 A1 | 7/2009 | Pan et al. |
| 2009/0206748 A1 | 8/2009 | Moriwaki et al. |
| 2009/0295274 A1 | 12/2009 | Hwang et al. |
| 2009/0302742 A1 | 12/2009 | Komori et al. |
| 2010/0108989 A1 | 5/2010 | Büsing et al. |
| 2010/0148161 A1 | 6/2010 | Kai et al. |
| 2010/0148162 A1 | 6/2010 | Komori et al. |
| 2010/0187505 A1 | 7/2010 | Stoessel et al. |
| 2010/0187506 A1 | 7/2010 | Park et al. |
| 2010/0187977 A1 | 7/2010 | Kai et al. |
| 2010/0187983 A1 | 7/2010 | Herron et al. |
| 2010/0213825 A1 | 8/2010 | Park et al. |
| 2010/0314644 A1 | 12/2010 | Nishimura et al. |
| 2011/0037062 A1 | 2/2011 | Fukumatsu et al. |
| 2011/0095269 A1 | 4/2011 | Zhang et al. |
| 2011/0095273 A1 | 4/2011 | Meng et al. |
| 2011/0121269 A1 | 5/2011 | Lecloux et al. |
| 2011/0127513 A1 | 6/2011 | Lee et al. |
| 2011/0147718 A1 | 6/2011 | Howard, Jr. et al. |
| 2011/0168992 A1 | 7/2011 | Bae et al. |

FOREIGN PATENT DOCUMENTS

| | | |
|---|---|---|
| CN | 1711334 A | 12/2005 |
| CN | 1768029 A | 5/2006 |
| CN | 1957646 A | 5/2007 |
| CN | 101076904 A | 11/2007 |
| CN | 101405255 A | 4/2009 |
| DE | 102005058557 A1 | 6/2007 |
| EP | 0443861 B1 | 5/1995 |
| EP | 681019 A2 | 9/1999 |
| EP | 1061112 A1 | 12/2000 |
| EP | 765106 A2 | 11/2002 |
| EP | 1277824 A1 | 1/2003 |
| EP | 1317005 A2 | 6/2003 |
| EP | 1437395 A2 | 7/2004 |
| EP | 1491609 A2 | 12/2004 |
| EP | 1491610 A2 | 12/2004 |
| EP | 1541657 A1 | 6/2005 |
| EP | 1561794 A1 | 8/2005 |
| EP | 1604974 A1 | 12/2005 |
| EP | 1612202 A1 | 1/2006 |
| EP | 1624500 A1 | 2/2006 |
| EP | 1672713 A1 | 6/2006 |
| EP | 1718124 A1 | 11/2006 |
| EP | 1737277 A1 | 12/2006 |
| EP | 1792893 A1 | 6/2007 |
| EP | 1860096 A1 | 11/2007 |
| EP | 1932895 A1 | 6/2008 |
| EP | 1933603 A1 | 6/2008 |
| EP | 1956022 A1 | 8/2008 |
| EP | 1995292 A1 | 11/2008 |
| EP | 2080762 A1 | 7/2009 |
| EP | 2085450 A1 | 8/2009 |
| EP | 2093271 A1 | 8/2009 |
| EP | 2067766 A1 | 10/2009 |
| EP | 2067767 A1 | 10/2009 |
| EP | 2189508 A2 | 5/2010 |
| JP | 04175395 A | 6/1992 |
| JP | 07249490 A | 9/1995 |
| JP | 08012600 A | 1/1996 |
| JP | 08053397 A | 2/1996 |
| JP | 08167479 A | 6/1996 |
| JP | 10251633 A | 9/1998 |
| JP | 11224779 A | 8/1999 |
| JP | 11338172 A | 12/1999 |
| JP | 2000068073 A | 3/2000 |
| JP | 2000186066 A | 7/2000 |
| JP | 2001039933 A | 2/2001 |
| JP | 2001226331 A | 8/2001 |
| JP | 2003026641 A | 1/2003 |
| JP | 2003238501 A | 8/2003 |
| JP | 2003297582 A | 10/2003 |
| JP | 2003338380 A | 11/2003 |
| JP | 2004-10550 A | 1/2004 |
| JP | 2004010550 A * | 1/2004 |
| JP | 2004014187 A | 1/2004 |
| JP | 2004071286 A | 3/2004 |
| JP | 2004107292 A | 4/2004 |
| JP | 2004224766 A | 8/2004 |
| JP | 2005015420 A | 1/2005 |
| JP | 2005232452 A | 9/2005 |
| JP | 2006016384 A | 1/2006 |
| JP | 2006052323 A | 2/2006 |
| JP | 2006-151844 A | 6/2006 |
| JP | 2006176493 A | 7/2006 |
| JP | 2006-219392 A | 8/2006 |
| JP | 2006328037 A | 12/2006 |
| JP | 2007-186449 A | 7/2007 |
| JP | 2007182432 A | 7/2007 |
| JP | 2007208165 A | 8/2007 |
| JP | 2008270737 A | 11/2008 |
| JP | 2008540517 A | 11/2008 |
| JP | 2009502778 A | 1/2009 |
| JP | 2009076865 A | 4/2009 |
| JP | 2009161470 A | 7/2009 |
| JP | 2009246354 A | 10/2009 |
| JP | 2011528033 A | 11/2011 |
| JP | 2012503027 A | 2/2012 |
| KR | 1020040079803 A | 9/2004 |
| KR | 1020050073233 A | 7/2005 |
| KR | 100702763 B1 | 4/2007 |
| KR | 1020070091293 A | 9/2007 |
| KR | 100765728 B1 | 10/2007 |
| KR | 10-2009-0046731 A | 5/2009 |
| KR | 10-2009-0086015 A | 8/2009 |
| KR | 10-2009-0086920 A | 8/2009 |
| KR | 10-2009-0093897 A | 9/2009 |
| WO | 9954385 A1 | 10/1999 |
| WO | 0053565 A1 | 9/2000 |
| WO | 0070655 A2 | 11/2000 |
| WO | 0141512 A1 | 6/2001 |
| WO | 02051958 A1 | 7/2002 |
| WO | 03008424 A1 | 1/2003 |
| WO | 03040257 A1 | 5/2003 |
| WO | 03063555 A1 | 7/2003 |
| WO | 03091688 A2 | 11/2003 |
| WO | 2004016710 A1 | 2/2004 |
| WO | 2004018587 A1 | 3/2004 |
| WO | 2004041901 A1 | 5/2004 |
| WO | 2004058913 A1 | 7/2004 |
| WO | 2005000787 A1 | 1/2005 |
| WO | 2005031889 A2 | 4/2005 |
| WO | 2005049546 A1 | 6/2005 |
| WO | 2005049548 A1 | 6/2005 |
| WO | 2005049689 A2 | 6/2005 |
| WO | WO2005/052027 A1 | 6/2005 |
| WO | 2005071773 A1 | 8/2005 |
| WO | 2005115950 A1 | 12/2005 |
| WO | 2006001333 A1 | 1/2006 |
| WO | 2006025273 A1 | 3/2006 |
| WO | 2006043087 A1 | 4/2006 |
| WO | 2006057326 A1 | 6/2006 |
| WO | 2006063852 A1 | 6/2006 |
| WO | 2006076146 A2 | 7/2006 |

(56) References Cited

FOREIGN PATENT DOCUMENTS

| WO | 2006082705 A1 | 8/2006 |
|---|---|---|
| WO | 2006085434 A1 | 8/2006 |
| WO | 2006086040 A2 | 8/2006 |
| WO | 2006090772 A1 | 8/2006 |
| WO | 2006112582 A1 | 10/2006 |
| WO | 2006121237 A1 | 11/2006 |
| WO | 2006137210 A1 | 12/2006 |
| WO | 2007004364 A1 | 1/2007 |
| WO | WO2007/021117 A1 | 2/2007 |
| WO | WO 2007021117 A1 * | 2/2007 |
| WO | 2007046658 A1 | 4/2007 |
| WO | 2007054345 A1 | 5/2007 |
| WO | 2007065678 A1 | 6/2007 |
| WO | 2007076146 A2 | 7/2007 |
| WO | 2007086695 A1 | 8/2007 |
| WO | 2007108457 A1 | 9/2007 |
| WO | 2007108666 A1 | 9/2007 |
| WO | WO2007-100096 A1 | 9/2007 |
| WO | WO2007-105917 A1 | 9/2007 |
| WO | WO2007-108666 A1 | 9/2007 |
| WO | 2007116828 A1 | 10/2007 |
| WO | 2007129702 A1 | 11/2007 |
| WO | 2008011953 A1 | 1/2008 |
| WO | 2008024378 A2 | 2/2008 |
| WO | 2008024379 A2 | 2/2008 |
| WO | 2008078114 A1 | 7/2008 |
| WO | 2008147721 A1 | 12/2008 |
| WO | 2008150828 A2 | 12/2008 |
| WO | WO2008-149968 A1 | 12/2008 |
| WO | WO2009/018009 A1 | 2/2009 |
| WO | WO2009/028902 A2 | 3/2009 |
| WO | WO2009-055628 A1 | 4/2009 |
| WO | 2009067419 A1 | 5/2009 |
| WO | 2009069790 A1 | 6/2009 |
| WO | 2010065494 A2 | 6/2010 |
| WO | 2010071362 A2 | 6/2010 |
| WO | 2010075421 A2 | 7/2010 |
| WO | 2010099534 A2 | 9/2010 |
| WO | 2010135403 A2 | 11/2010 |
| WO | 2011053334 A1 | 5/2011 |

OTHER PUBLICATIONS

"Flexible light-emitting diodes made from soluble conducting polymer" Nature, vol. 357, pp. 477 479 (Jun. 11, 1992).

Kirk-Othmer Encyclopedia of Chemical Technology, Fourth Edition, vol. 18, pp. 837-860, 1996 Y. Wang.

Markus, John, Electronics and Nucleonics dictionary, 470 and 476 (McGraw-Hill 1966).

"Efficient H/D Exchange Reactions of Alkyl-Substituted Benzene Derivatives by Means of the Pd/C—H2—D2O System" Hiroyoshi Esaki, Fumiyo Aoki, Miho Umemura, Masatsugu Kato, Tomohiro Maegawa, Yasunari Monguchi, and Hironao Sajiki Chem. Eur. J. 2007, 13, 4052-4063.

"Aromatic H/D Exchange Reaction Catalyzed by Groups 5 and 6 Metal Chlorides" Guo, Qiao-Xia, Shen, Bao-Jian; Guo, Hai-Qing Takahashi, Tamotsu Chinese Journal of Chemistry, 2005, 23, 341-344.

"A novel deuterium effect on dual charge-transfer and ligand-field emission of the cis-dichlorobis(2,2'-bipyridine)iridium(III) ion" Richard J. Watts, Shlomo Efrima, and Norio Metiu J. Am. Chem. Soc., 1979, 101 (10), 2742-2743.

"Efficient H-D Exchange of Aromatic Compounds in Near-Critical D20 Catalysed by a Polymer-Supported Sulphonic Acid" Carmen Boix and Martyn Poliakoff Tetrahedron Letters 40 (1999) 4433-4436.

"Efficient C—H/C—D Exchange Reaction on the Alkyl Side Chain of Aromatic Compounds Using Heterogeneous Pd/C in D20" Hironao Sajiki, Fumiyo Aoki, Hiroyoshi Esaki, Tomohiro Maegawa, and Kosaku Hirota Org. Lett., 2004, 6 (9), 1485-1487.

Beckmann et al., "Methyl Reorientation in Solid 3-ethychrysene and 3-isopropylesene; Solid State Nuclear Magnetic Resonance," 1998; vol. 12; pp. 251-256.

Carey et al., Structure and Mechanisms; Advanced Organic Chemistry, Part A, 5th Edition, pp. 142-145, Jun. 13, 2007.

Chu et al., "Comparitive Study of Single and Multiemissive Layers in Inverted White Organic Light-Emitting Devices," Applied Physics Letters, 2006, vol. 89, No. 11, p. 113502.

Danel et al., "Blue-Emitting Anthracenes with End-Capping Diarylamines," Chem. Mater., 2002, vol. 14, pp. 3860-3865.

Eaton et al., "Dihedral Angle of Biphenyl in Solution and the Molecular Force Field," J. Chem. Soc. Faraday Trans. 2, 1973, 60 pp. 1601-1608.

Hartwig, "Carbon-Heteroatom Bond Formation Catalyzed by Organometallic Complexes," Nature, 2008 vol. 455, No. 18, pp. 314-322.

Hartwig, "Discovery and Understanding of Transition-Metal-Catalyzed Aromatic Substitution Reactions," Syn Lett., 2006, No. 9, pp. 1283-1294.

Ishiyama et al., "Palladium(0)-Catalyzed Cross-Coupling Reaction of Alkoxydiboron with Haloarenes: A Direct Procedure for Arylboronic Esters," Journal of Organic Chemistry, 1995, vol. 60, pp. 7508-7510.

Kim et al., "Synthesis and Electroluminescent Properties of Highly Efficient Anthracene Derivatives with Bulky Side Groups," Organic Electronics, 2009, vol. 10, No. 5, pp. 822-833.

Klaerner et al., "Cross-Linkable Polymers Based on Dialkylfluorenes," Chemistry of Materials, 1999, 11, pp. 1800-1805.

Kodomari et al., "Selective Halogenation of Aromatic Hydrocarbons," Journal of Organic Chemistry, 1988, vol. 53, p. 2093.

Kumada, "Nickel and Palladium Complex Catalyzed Cross-Coupling Reactions of Organometallic Reagents with Organic Halides," Pure & Applied Chemistry, 1980, vol. 52, pp. 669-679.

Leznoff et al "Photocyclization of Aryl Polyenes. V. Photochemical Synthesis of Substituted Chrysenes," Canadian Journal of Chemistry, 1972, vol. 50, pp. 528-533.

Mueller et al., "Synthesis and Characterization of Soluble Oligo(9,10-anthrylene)s," Chemische Berichte, 1994, 127, pp. 437-444.

Murata et al., "Novel Palladium(0)-Catalyzed Coupling Reaction of Dialkoxyborane with Aryl Halides: A Convenient Synthetic Route to Arylboronates," Journal of Organic Chemistry, 1997, vol. 62, pp. 6458-6459.

Murata et al., "Palladium-Catalyzed Borylation of Aryl Halides or Triflates with Dialkoxyborane: A Novel and Facile Synthetic Route to Aryboronates," Journal of Organic Chemistry, 2000, vol. 65, No. 1, pp. 164-168.

Negishi et al; III.2.15 Palladium Catalyzed Conjugate Substitution; Handbook of Organopalladium Chemistry for Organic Synthesis, 2000, vol. 1, pp. 767-789.

Negishi, "Palladium- or Nickel-Catalyzed Cross Coupling. A New Selective Method for Carbon-Carbon Bond Formation,"Accounts of Chemical Research, 1982, vol. 15, pp. 340-348.

Stille, "The Palladium-Catalyzed Cross-Coupling Reactions of Organotin Reagents with Organic Electrophiles," Angew. Chem. Int. Ed. Engl., 1986, vol. 25, pp. 508-524.

Tong et al., "Enhancement of OLED Efficiencies and High-Voltage Stabilities of Light-Emitting Materials by Deuteration," Journal of Physical Chemistry, 2007, vol. 111, pp. 3490-3494.

Wang et al., "Novel bis(8-hydroxyquinoline)phenolate-aluminum Complexes for Organic Light-emitting Diodes," Synthetic Metals, 2002, vol. 131, 1-3, pp. 1-5.

Weine et al., "Reactions of an O-Quinone Monoimide with Anthracenes, Phencyclone, and 1,3-Diphenylisobenzofuran," Journal of Organic Chemistry, 1989, vol. 54, pp. 5926-5930.

Wellmann et al., "High-Efficiency p-i-n Organic Light-Emitting Diodes with Long Lifetime," Journal of the SID, 2005, vol. 13/5, pp. 393-397.

Yamada et al., Synthesis of 2,9-Dichloro-1,10-phenanthroline from N,N'-Annelated Phenanthrolinediones, Bulletin of the Chemical Society of Japan, 1990, vol. 63, No. 9, pp. 2710-2712.

Yamamoto et al., "Electrically conducting and thermally stable □-conjugated poly(arylene)s prepared by organometallic process," Progress in Polymer Science, 1992, vol. 17, pp. 1153-1205.

(56) References Cited

OTHER PUBLICATIONS

Yan et al., "Synthesis and Nonlinear Optical Properties of Novel Multi-branched Two-Photon Polymerization Initiators," Journal of Material Chemistry, 2004, vol. 14, pp. 2295-3000.
Zhu et al., "An Improved Preparation of Arylboronates: Application in One-Pot Suzuki Biaryl Synthesis," Journal of Organic Chemistry, 2003, vol. 68, pp. 3729-3732.
Extended European Search Report for Application No. 10746974.4, counterpart to U.S. Appl. No. 12/714,880; EPO; Nov. 5, 2012.
Extended European Search Report for Application No. 10778305.2, counterpart to U.S. Appl. No. 12/782,781; EPO; Nov. 5, 2012.
Extended European Search Report for Application No. 12166882.6; Jul. 18, 2012.
Extended European Search Report for Application No. EP 09844464.9, counterpart to U.S. Appl. No. 12/643,511; Oct. 26, 2012.
First Official Action; EPO; Application No. 08756397.9; Oct. 27, 2011.
Official Action; EPO; Application No. 08756397.9, counterpart to U.S. Appl. No. 12/129,785; Jul. 17, 2012.
PCT International Search Report for Application No. PCT/US2008/065016, counterpart to U.S. Appl. No. 12/129,785; M. Redecker, Authorized Officer, Oct. 12, 2008.
PCT International Search Report for Application No. PCT/US2009/068922, counterpart to U.S. Appl. No. 12/643,567; Oh Hyun Shik, Authorized Officer; KIPO; Oct. 2010.
PCT International Search Report for Application No. PCT/US2009/068928, counterpart to U.S. Appl. No. 12/643,511; Oh Hyun Shik, Authorized Officer; KIPO; Aug. 17, 2010.
PCT International Search Report for Application No. PCT/US2009/068945, counterpart to U.S. Appl. No. 12/643,420; Oh Hyun Shik, Authorized Officer; KIPO; Sep. 27, 2010.
PCT International Search Report for Application No. PCT/US2009/068950, counterpart to U.S. Appl. No. 12/643,449; Oh Hyun Shik, Authorized Officer; KIPO; Jan. 3, 2011.
PCT International Search Report for Application No. PCT/US2009/068956, counterpart to U.S. Appl. No. 12/643,487; Oh Hyun Shik, Authorized Officer; KIPO; Sep. 6, 2010.
PCT International Search Report for Application No. PCT/US2009/068976, counterpart to U.S. Appl. No. 12/643,515; Kim Bum Soo, Authorized Officer; KIPO; Jan. 28, 2011.
PCT International Search Report for Application No. PCT/US2009/069255, counterpart to U.S. Appl. No. 12/643,459; Oh Hyun Shik, Authorized Officer; KIPO; Aug. 13, 2010.
PCT International Search Report for Application No. PCT/US2010/025764, counterpart to U.S. Appl. No. 12/714,880; Oh Hyun Shik, Authorized Officer; KIPO; Sep. 27, 2010.
PCT International Search Report for Application No. PCT/US2010/035356, counterpart to U.S. Appl. No. 12/782,781; Oh Hyun Shik, Authorized Officer; KIPO; Dec. 24, 2010.
PCT International Search Report for Application No. PCT/US2010/061672, counterpart to U.S. Appl. No. 12/643,381; Kim, Dongseok, Authorized Officer; KIPO; Sep. 26, 2011.
PCT International Search Report for Application No. PCT/US2011/065789; Asgeir Konradsson, Authorized Officer; EPO; Mar. 14, 2012.
PCT International Search Report for Application No. PCT/US2011/065802; Stephan Heer, Authorized Officer; EPO; May 11, 2012.
PCT International Search Report for Application No. PCT/US2011/065818; Asgeir Konradsson, Authorized Officer; EPO; Mar. 14, 2012.
"Color." (Definition) Web. Sep. 27, 2011, <http://hyperphysics.phy-astr.gsu/Hbase/vision/secpl>.
Appleby et al., Polymeric Perfluoro Bis-Sulfanomides as Possible Fuel Cell Electrolytes, J. Electrochem. Soc., 1993, vol. 140, pp. 109-111.
Borello et al., "Photodetectors," Kirk-Othmer Encyclopedia of Chemical Technology, Fourth Edition, 1999, vol. 18, pp. 1537-1538.
Braun et al., "Visible Light Emission from Semiconducting Polymer Diodes," Applied Physics Letters, 1991, vol. 58 (18), pp. 1982-1984.
Chen et al., "Efficient, Blue Light-Emnitting Diodes Using Cross-Linked Layers of Polymeric Arylamine and Fluorene," Synthetic Metals, 1999, vol. 107, pp. 129-138.
Chu et al., "Highly Efficient and Stable Inverted Bottom-Emission Organic Light Emitting Devices," Applied Physics Letters, 2006, vol. 89, pp. 053503-1 to 053503-3.
Colon et al., "High Molecular Weight Aromatic Polymers by Nickel Coupling of Aryl Polychlorides," Journal of Polymer Science, Part A, Polymer Chemistry Edition, 1990, vol. 28, pp. 367-383.
Constantini et al., "Infrared Spectroscopic Study of Polaron Formation in Electrochemically Synthesized Poly(3-alkylpyrroles)," Phys. Chem. Chem. Phys., 2003, vol. 5, pp. 749-757.
Desmarteau, "Novel Perfluorinated Ionomers and Ionenes," Journal of Fluorine Chemistry, 1995, vol. 72, pp. 203-208.
Feiring et al., "Aromatic Monomers with Pendant Fluoroalkylsulfonate and Sulfonimide Groups," Journal of Fluorine Chemistry, 2000, vol. 105, pp. 129-135.
Feiring et al., "Novel Aromatic Polymers with Pendant Lithium Perfluoroalkylsulfonate or Sulfinimide Groups," Macromolecules, 2000, vol. 33, pp. 9262-9271.
He et al., "A Hole-transporting material with Controllable Morphology Containing Binaphthyl and Triphenylamine Chromophores," Advanced Functional Materials, 2006, vol. 16, No. 10, pp. 1343-1348.
He et al., "High-efficiency Organic Polymer Light-emitting Heterostructure Devices on Flexible Plastic Substrates," Applied Physics Letters, 2000, vol. 76, No. 6, pp. 661-663.
Lee et al., "A Thermally Stable Hole Injection Material for Use in Organic Light-Emitting Diodes," Thin Solid Films, 2007, vol. 515, pp. 7726-7731.
Lee et al., "Poly(thieno(3,4-b)thiophene) A New Stable Low Band Gap Conducting Polymer," Macromolecules, 2001, vol. 34, pp. 5746-5747.
Maeda et al., "Alkynylpyrenes as Improved Pyrene-Based Biomolecular Probes with the Advantages of High Fluorescence Quantum Yields and Long Absorption/Emission Wavelengths," Chemisty—A European Journal, 2006, vol. 12(3), pp. 824-831.
March, Aromatization of Six-Membered Rings, Advanced Organic Chemistry, Wiley-Interscience (1992), 4th Ed., pp. 1162-1164.
Minabe et al., "Electrophilic Substitution of Monosubstituted Pyrenes," Bulletin of the Chemical Society of Japan, 1994, vol. 67(1), pp. 172-179.
Noji et al., "A New Catalytic System for Aerobic Oxidative Coupling of 2-Naphthol Derivatives by the Use of CuCl-Amine Complex: A Practical Synthesis of Binaphthol Derivatives," Tetrahedron Letters, 1994, vol. 35, No. 43, pp. 7983-7984.
Norman et al., "The Reactions of Pyrene with Free Radicals and with Sodium," Journal of the Chemical Society, 1958, pp. 175-179.
Park et al., "Ab Initio Study of Pyrenes for Blue Organic Light-Emitting Diodes," Molecular Crystals and Liquid Crystals, 2006, vol. 444, pp. 177-184.
Sheldon et al., "The Mechanism of the Collision-induced Loss of Methane from the Trimethylsilyl Negative Ion," Perkin Transaction II: Organic and Bio-Organic Chemistry, Journal of the Chemical Society, 1988, vol. 7, pp. 1263-1268.
Sotzing et al., "Poly(thieno(3,4-b)thiophene): A p- and n-Dopable Polythiophene Exhibiting High Optical Transparency in the Semiconducting State," Macromolecules, 2002, vol. 35, pp. 7281-7286.
Sze, S.M., Physics of Semiconductor Devices, 2nd Edition, 1981, John Wiley & Sons, p. 492.
Tokito et al., "Highly Efficient Blue-Green Emission from Organic Light-Emitting Diodes Using Dibenzochrysene Derivatives," Applied Physics Letters, 2000, vol. 77, No. 2, pp. 160-162.
Zhao et al., "Solid-State Dye-Sensitized Photovoltaic Device with Newly Designed Small Organic Molecule as Hole-Conductor," Chemical Physical Letters, 2007, vol. 445, pp. 259-264.
Zhu et al., "Effect of ITO Carrier Concentration on the Performance of Light-Emitting Diodes," 2000; Material Research Society; Chem Abstract 134: 122994.
Extended European Search Report for Application No. 09848342.3, counterpart to U.S. Appl. No. 12/643,487; Jan. 23, 2013.
Extended European Search Report for Application No. 09849078.2, counterpart to U.S. Appl. No. 12/643,420; Jan. 11, 2013.

(56) References Cited

OTHER PUBLICATIONS

Non-Final Office Action mailed Apr. 4, 2012, in U.S. Appl. No. 12/714,880.

Final Office Action mailed Oct. 17, 2012, in U.S. Appl. No. 12/714,880.

Non-Final Office Action mailed May 10, 2012, in U.S. Appl. No. 12/782,781.

Final Office Action mailed Oct. 16, 2012, in U.S. Appl. No. 12/782,781.

Biehl et al., "ESR, NMR, and ENDOR Studies of Partially Deuterated Phenyl Substituted Anthracenes, $\pi$—$\sigma$ Delocalization," Journal of the American Chemical Society, 1977, vol. 99, No. 13, pp. 4278-4286.

Ge et al., "Novel Bipolar Bathophenanthroline Containing Hosts for Highly Efficient Phosphorescent OLEDs," Organic Letters, 2008, vol. 10, No. 3, pp. 421-424.

* cited by examiner

DEUTERATED COMPOUNDS FOR ELECTRONIC APPLICATIONS

RELATED APPLICATION DATA

This application claims priority under 35 U.S.C. §119(e) from U.S. Provisional Application No. 61/156,181 filed on Feb. 27, 2009(now U.S. application Ser. No. 12/714,880), U.S. Provisional Application No. 61/179,407 filed on May 19, 2009(now U.S. application Ser. No. 12/782,781), and U.S. Provisional Application No. 61/239,574 filed on Sep. 3, 2009, each of which is incorporated by reference herein in its entirety.

BACKGROUND

1. Field of the Disclosure

This invention relates to anthracene derivative compounds which are at least partially deuterated. It also relates to electronic devices in which at least one active layer includes such a compound.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. No. 5,247,190, U.S. Pat. No. 5,408,109, and Published European Patent Application 443 861. In many cases the electroluminescent compound is present as a dopant in a host material.

There is a continuing need for new materials for electronic devices.

SUMMARY

There is provided an aryl-substituted anthracene having at least one deuterium substituent.

There is also provided an electronic device comprising an active layer comprising the above compound.

There is further provided an electroactive composition comprising (a) an aryl-substituted anthracene having at least one deuterium substituent and (b) an electroactive dopant capable of electroluminescence having an emission maximum between 380 and 750 nm.

BRIEF DESCRIPTION OF THE DRAWINGS

Embodiments are illustrated in the accompanying figures to improve understanding of concepts as presented herein.

Figure 1:
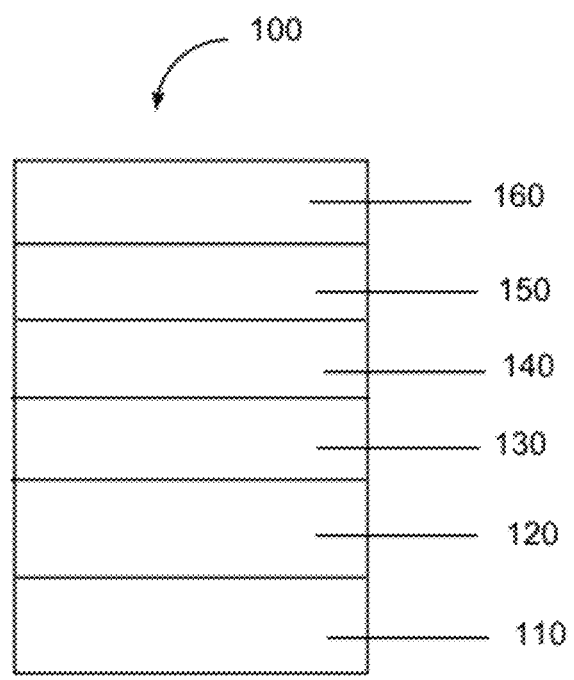
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are disclosed herein and are exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Deuterated Compound, the Electronic Device, and finally Examples.

1. DEFINITIONS AND CLARIFICATION OF TERMS

Before addressing details of embodiments described below, some terms are defined or clarified.

As used herein, the term "aliphatic ring" is intended to mean a cyclic group that does not have delocalized pi electrons. In some embodiments, the aliphatic ring has no unsaturation. In some embodiments, the ring has one double or triple bond.

The term "alkoxy" refers to the group RO—, where R is an alkyl.

The term "alkyl" is intended to mean a group derived from an aliphatic hydrocarbon having one point of attachment, and includes a linear, a branched, or a cyclic group. The term is intended to include heteroalkyls. The term "hydrocarbon alkyl" refers to an alkyl group having no heteroatoms. The term "deuterated alkyl" is a hydrocarbon alkyl having at least one available H replaced by D. In some embodiments, an alkyl group has from 1-20 carbon atoms.

The term "branched alkyl" refers to an alkyl group having at least one secondary or tertiary carbon. The term "secondary alkyl" refers to a branched alkyl group having a secondary carbon atom. The term "tertiary alkyl" refers to a branched alkyl group having a tertiary carbon atom. In some embodiments, the branched alkyl group is attached via a secondary or tertiary carbon.

The term "aryl" is intended to mean a group derived from an aromatic hydrocarbon having one point of attachment. The term "aromatic compound" is intended to mean an organic compound comprising at least one unsaturated cyclic group having delocalized pi electrons. The term is intended include heteroaryls. The term "hydrocarbon aryl" is intended to mean aromatic compounds having no heteroatoms in the ring. The term aryl includes groups which have a single ring and those which have multiple rings which can be joined by a single bond or fused together. The term "deuterated aryl" refers to an aryl group having at least one available H bonded directly to the aryl replaced by D. The term "arylene" is intended to mean a group derived from an aromatic hydrocarbon having two points of attachment. In some embodiments, an aryl group has from 3-60 carbon atoms.

The term "aryloxy" refers to the group RO—, where R is an aryl.

The term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "deuterated" is intended to mean that at least one H has been replaced by D. The deuterium is present in at least 100 times the natural abundance level. A "deuterated derivative" of compound X has the same structure as compound X, but with at least one D replacing an H.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, planarization materials, insulating materials, and environmental barrier materials.

The prefix "hetero" indicates that one or more carbon atoms have been replaced with a different atom. In some embodiments, the different atom is N, O, or S.

The term "host material" is intended to mean a material to which a dopant is added. The host material may or may not have electronic characteristic(s) or the ability to emit, receive, or filter radiation. In some embodiments, the host material is present in higher concentration.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device" or sometimes just "electronic device" is intended to mean a device including one or more organic semiconductor layers or materials. All groups can be substituted or unsubstituted unless otherwise indicated. In some embodiments, the substituents are selected from the group consisting of D, halide, alkyl, alkoxy, aryl, aryloxy, cyano, and $NR_2$, where R is alkyl or aryl.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81st Edition, 2000).

2. DEUTERATED COMPOUND

The new deuterated compound is an aryl-substituted anthracene compound having at least one D. In some embodiments, the compound is at least 10% deuterated. By this is meant that at least 10% of the H are replaced by D. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the compounds are 100% deuterated.

In one embodiment, the deuterated compound has Formula I:

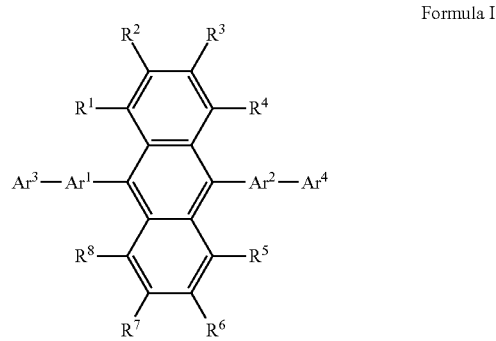

Formula I wherein:
  $R^1$ through $R^8$ are the same or different at each occurrence and are selected from the group consisting of H, D, alkyl, alkoxy, aryl, aryloxy, siloxane, and silyl;
  $Ar^1$ and $Ar^2$ are the same or different and are selected from the group consisting of aryl groups; and
  $Ar^3$ and $Ar^4$ are the same or different and are selected from the group consisting of H, D, and aryl groups;
wherein the compound has at least one D.

In some embodiments of Formula I, the at least one D is on a substituent group on an aryl ring. In some embodiments, the substituent group is selected from alkyl and aryl.

In some embodiments of Formula I, at least one of $R^1$ through $R^8$ is D. In some embodiments, at least two of $R^1$ through $R^8$ are D. In some embodiments, at least three are D; in some embodiments, at least four are D; in some embodiments, at least five are D; in some embodiments, at least six are D; in some embodiments, at least seven are D. In some embodiments, all of $R^1$ through $R^8$ are D.

In some embodiments, $R^1$ through $R^8$ are selected from H and D. In some embodiments, one of $R^1$ through $R^8$ are D and seven are H. In some embodiments, two of $R^1$ through $R^8$ are D and six are H. In some embodiments, three of $R^1$ through $R^8$ are D and five are H. In some embodiments, four of $R^1$ through $R^8$ are D, and four are H. In some embodiments, five of $R^1$ through $R^8$ are D and three are H. In some embodiments, six of $R^1$ through $R^8$ are D and two are H. In some embodiments, seven of $R^1$ through $R^8$ are D and one is H. In some embodiments, eight of $R^1$ through $R^8$ are D.

In some embodiments, at least one of $R^1$ through $R^8$ is selected from alkyl, alkoxy, aryl, aryloxy, siloxane, and silyl, and the remainder of $R^1$ through $R^8$ are selected from H and D. In some embodiments, $R^2$ is selected from alkyl, alkoxy, aryl, aryloxy, siloxane, and silyl. In some embodiments, $R^2$ is selected from alkyl and aryl. In some embodiments, $R^2$ is selected from deuterated alkyl and deuterated aryl. In some embodiments, $R^2$ is selected from deuterated aryl having at least 10% deuteration. In some embodiments, $R^2$ is selected from deuterated aryl having at least 20% deuteration; in some embodiments, at least 30% deuteration; in some embodiments, at least 40% deuteration; in some embodiments, at least 50% deuteration; in some embodiments, at least 60% deuteration; in some embodiments, at least 70% deuteration; in some embodiments, at least 80% deuteration; in some embodiments, at least 90% deuteration. In some embodiments, $R^2$ is selected from deuterated aryl having 100% deuteration.

In some embodiments of Formula I, at least one of $Ar^1$ through $Ar^4$ is a deuterated aryl. In some embodiments, $Ar^3$ and $Ar^4$ are selected from D and deuterated aryls.

In some embodiments of Formula I, $Ar^1$ through $Ar^4$ are at least 10% deuterated. In some embodiments of Formula I, $Ar^1$ through $Ar^4$ are at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, the compound of Formula I is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the compound is 100% deuterated.

In some embodiments, $Ar^1$ and $Ar^2$ are selected from the group consisting of phenyl, naphthyl, phenanthryl, anthracenyl, and deuterated derivatives thereof. In some embodiments, $Ar^1$ and $Ar^2$ are selected from the group consisting of phenyl, naphthyl, and deuterated derivatives thereof.

In some embodiments, $Ar^3$ and $Ar^4$ are selected from the group consisting of phenyl, naphthyl, phenanthryl, anthracenyl, phenylnaphthylene, naphthylphenylene, deuterated derivatives thereof, and a group having Formula II:

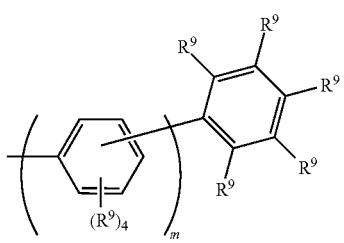

Formula II where:
$R^9$ is the same or different at each occurrence and is selected from the group consisting of H, D, alkyl, alkoxy, siloxane and silyl, or adjacent $R^9$ groups may be joined together to form an aromatic ring; and
m is the same or different at each occurrence and is an integer from 1 to 6.

In some embodiments, $Ar^3$ and $Ar^4$ are selected from the group consisting of phenyl, naphthyl, phenylnaphthylene, naphthylphenylene, deuterated derivatives thereof, and a group having Formula III:

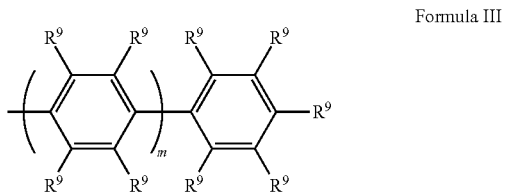

Formula III where $R^9$ and m are as defined above for Formula II. In some embodiments, m is an integer from 1 to 3.

In some embodiments, at least one of $Ar^1$ through $Ar^4$ is a heteroaryl group. In some embodiments, the heteroaryl group is deuterated. In some embodiments, the heteroaryl group is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the heteroaryl group is 100% deuterated. In some embodiments, the heteroaryl group is selected from carbazole, benzofuran, dibenzofuran, and deuterated derivatives thereof.

In some embodiments of Formula I, at least one of $R^1$ through $R^8$ is D and at least one of $Ar^1$ through $Ar^4$ is a deuterated aryl. In some embodiments, the compound is at least 10% deuterated. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the compound is 100% deuterated.

Some non-limiting examples of compounds having Formula I include Compounds H1 through H14 below:

Compound H1:

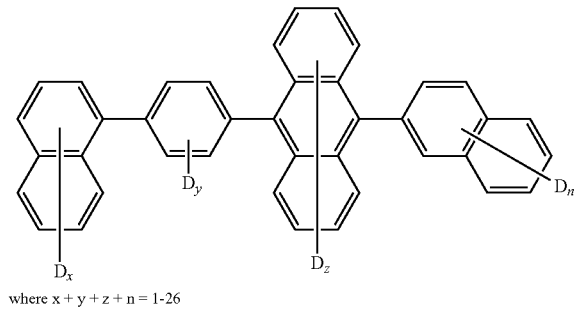

where $x + y + z + n = 1$-$26$

Compound H2:
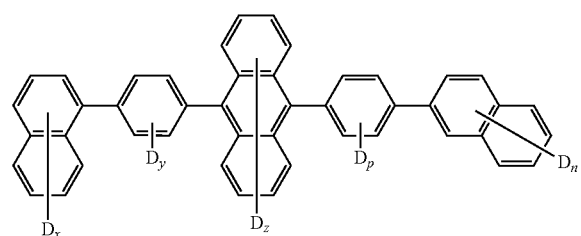
where x + y + z + p + n = 1-30
Compound H3:
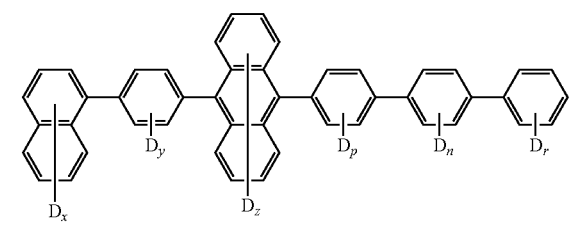
where x + y + z + p + n + r = 1-32
Compound H4:
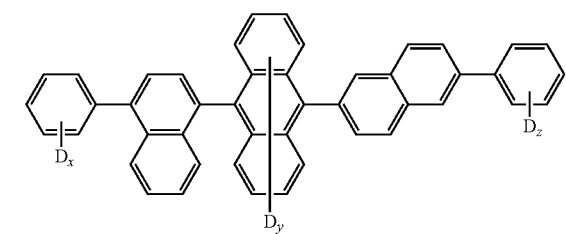
where x + y + z + p + n = 1-18
Compound H5:
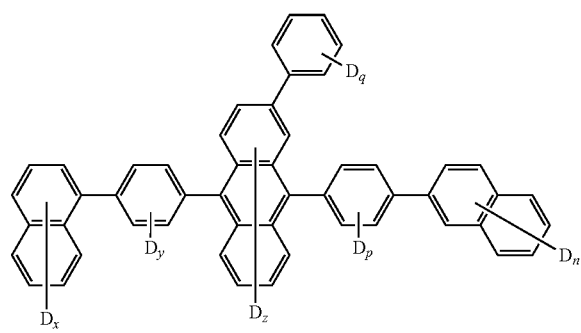
where x + y + z + p + n + q = 1-34
Compound H6:
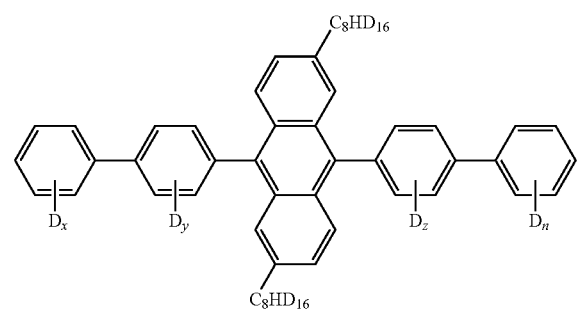
where x + y + z + n = 1-18
Compound H7:
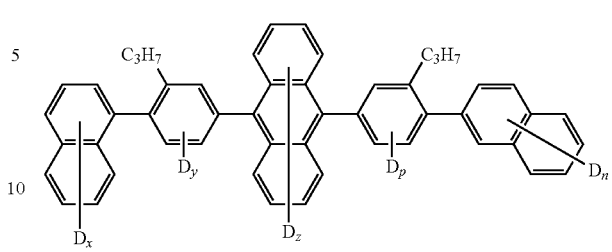
where x + y + z + p + n = 1-28
Compound H8:
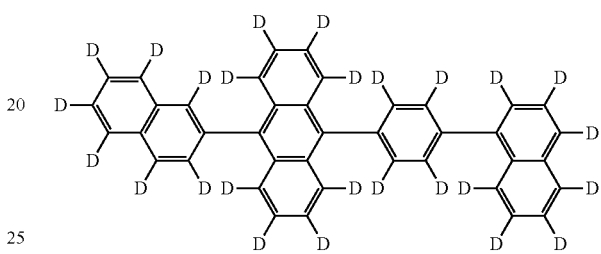
Compound H9:
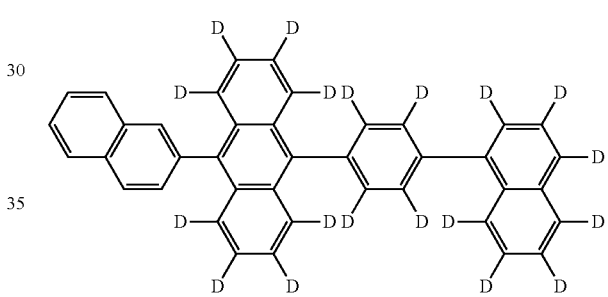
Compound H10:
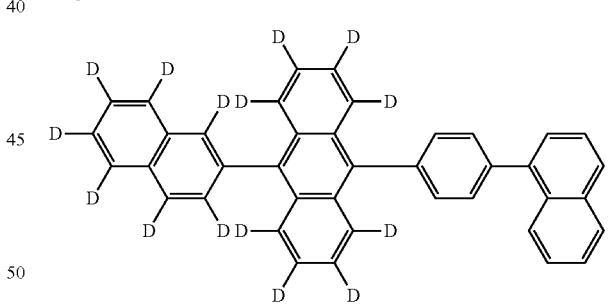
Compound H11:
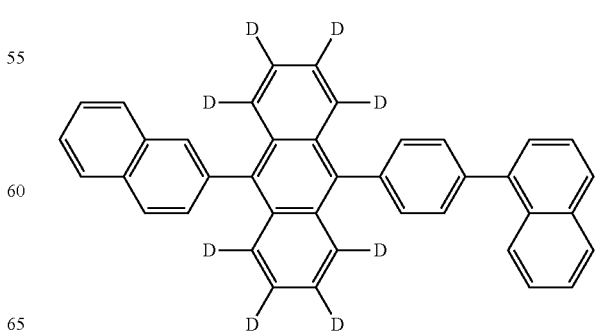

-continued

Compound H12:

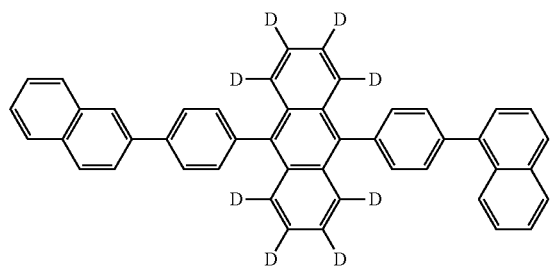

Compound H13:

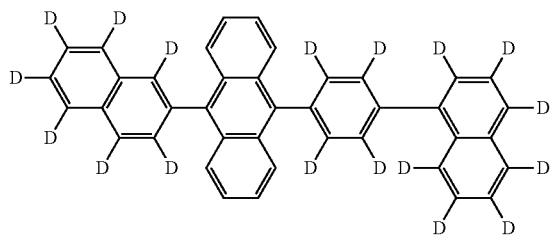

Compound H14:

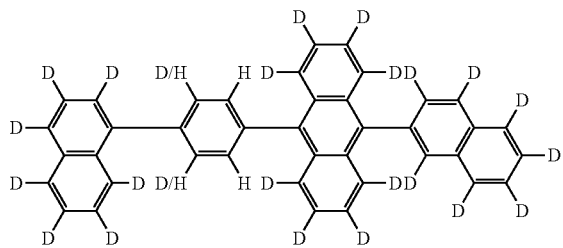

The non-deuterated analogs of the new compounds can be prepared by known coupling and substitution reactions. The new deuterated compound can then be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Exemplary preparations are given in the Examples. The level of deuteration can be determined by NMR analysis and by mass spectrometry, such as Atmospheric Solids Analysis Probe Mass Spectrometry (ASAP-MS). The starting materials of the perdeuterated or partially deuterated aromatic compounds or alky compounds can be purchased from the commercial source or can be obtained using known methods. Some examples of such methods can be found in a) "Efficient H/D Exchange Reactions of Alkyl-Substituted Benzene Derivatives by Means of the Pd/C—H2-D2O System" Hiroyoshi Esaki, Fumiyo Aoki, Miho Umemura, Masatsugu Kato, Tomohiro Maegawa, Yasunari Monguchi, and Hironao Sajiki Chem. Eur. J. 2007, 13, 4052-4063. b) "Aromatic H/D Exchange Reaction Catalyzed by Groups 5 and 6 Metal Chlorides" GUO, Qiao-Xia, SHEN, Bao-Jian; GUO, Hai-Qing TAKAHASHI, Tamotsu Chinese Journal of Chemistry, 2005, 23, 341-344; c) "A novel deuterium effect on dual charge-transfer and ligand-field emission of the cis-dichlorobis(2,2'-bipyridine)iridium(III) ion" Richard J. Watts, Shlomo Efrima, and Horia Metiu J. Am. Chem. Soc., 1979, 101 (10), 2742-2743; d) "Efficient H-D Exchange of Aromatic Compounds in Near-Critical D2O Catalysed by a Polymer-Supported Sulphonic Acid" Carmen Boix and Martyn Poliakoff Tetrahedron Letters 40 (1999) 4433-4436; e) U.S. Pat. No. 3,849,458; f) "Efficient C—H/C-D Exchange Reaction on the Alkyl Side Chain of Aromatic Compounds Using Heterogeneous Pd/C in D2O" Hironao Sajiki, Fumiyo Aoki, Hiroyoshi Esaki, Tomohiro Maegawa, and Kosaku Hirota Org. Lett., 2004, 6 (9), 1485-1487.

The compounds described herein can be formed into films using liquid deposition techniques. Surprisingly and unexpectedly, these compounds have greatly improved properties when compared to analogous non-deuterated compounds. Electronic devices including an active layer with the compounds described herein, have greatly improved lifetimes. In addition, the lifetime increases are achieved in combination with high quantum efficiency and good color saturation. Furthermore, the deuterated compounds described herein have greater air tolerance than the non-deuterated analogs. This can result in greater processing tolerance both for the preparation and purification of the materials and in the formation of electronic devices using the materials.

3. ELECTRONIC DEVICE

Organic electronic devices that may benefit from having one or more layers comprising the electroluminescent materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and an electroactive layer 140 between them. Adjacent to the anode may be a hole injection layer 120. Adjacent to the hole injection layer may be a hole transport layer 130, comprising hole transport material. Adjacent to the cathode may be an electron transport layer 150, comprising an electron transport material. Devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 130, 50-2000 Å, in one embodiment 200-1000 Å; electroactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the electroactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

One or more of the new deuterated materials described herein may be present in one or more of the active layers of a device. The deuterated materials may be used alone or in combination with non-deuterated materials.

In some embodiments, the new deuterated compounds are useful as hole transport materials in layer 130. In some embodiments, at least one additional layer includes a new deuterated material. In some embodiments, the additional layer is the hole injection layer 120. In some embodiments, the additional layer is the electroactive layer 140. In some embodiments, the additional layer is the electron transport layer 150.

In some embodiments, the new deuterated compounds are useful as host materials for electroactive dopant materials in electroactive layer 140. In some embodiments, the emissive material is also deuterated. In some embodiments, at least one additional layer includes a deuterated material. In some embodiments, the additional layer is the hole injection layer 120. In some embodiments, the additional layer is the hole transport layer 130. In some embodiments, the additional layer is the electron transport layer 150

In some embodiments, the new deuterated compounds are useful as electron transport materials in layer 150. In some embodiments, at least one additional layer includes a deuterated material. In some embodiments, the additional layer is the hole injection layer 120. In some embodiments, the additional layer is the hole transport layer 130. In some embodiments, the additional layer is the electroactive layer 140.

In some embodiments, an electronic device has deuterated materials in any combination of layers selected from the group consisting of the hole injection layer, the hole transport layer, the electroactive layer, and the electron transport layer.

In some embodiments, the devices have additional layers to aid in processing or to improve functionality. Any or all of these layers can include deuterated materials. In some embodiments, all the organic device layers comprise deuterated materials. In some embodiments, all the organic device layers consist essentially of deuterated materials.

a. Electroactive Layer

The new deuterated compounds of Formula I are useful as host materials for electroactive dopant materials in layer 140. The compounds can be used alone, or in combination with a second host material. The new deuterated compounds can be used as a host for dopants with any color of emission. In some embodiments, the new deuterated compounds are used as hosts for green- or blue-emissive materials.

In some embodiments, the electroactive layer consists essentially of a host material having Formula I and one or more electroactive dopants. In some embodiments, the electroactive layer consists essentially of a first host material having Formula I, a second host material, and an electroactive dopant. Examples of second host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes.

The amount of dopant present in the electroactive composition is generally in the range of 3-20% by weight, based on the total weight of the composition; in some embodiments, 5-15% by weight. When a second host is present, the ratio of first host having Formula I to second host is generally in the range of 1:20 to 20:1; in some embodiments, 5:15 to 15:5. In some embodiments, the first host material having Formula I is at least 50% by weight of the total host material; in some embodiments, at least 70% by weight.

In some embodiments, the second host material has Formula IV:

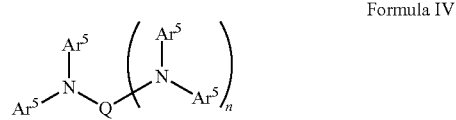

Formula IV where:
Ar$^5$ is the same or different at each occurrence and is an aryl group;
Q is selected from the group consisting of multivalent aryl groups and

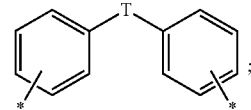

T is selected from the group consisting of $(CR')_a$, $SiR_2$, S, $SO_2$, PR, PO, $PO_2$, BR, and R;
R is the same or different at each occurrence and is selected from the group consisting of alkyl, and aryl;
R' is the same or different at each occurrence and is selected from the group consisting of H and alkyl;
a is an integer from 1-6; and
n is an integer from 0-6.

While n can have a value from 0-6, it will be understood that for some Q groups the value of n is restricted by the chemistry of the group. In some embodiments, n is 0 or 1.

In some embodiments of Formula IV, adjacent Ar groups are joined together to form rings such as carbazole. In Formula IV, "adjacent" means that the Ar groups are bonded to the same N.

In some embodiments, Ar$^5$ is independently selected from the group consisting of phenyl, biphenyl, terphenyl, quaterphenyl, naphthyl, phenanthryl, naphthylphenyl, and phenanthrylphenyl. Analogs higher than quaterphenyl, having 5-10 phenyl rings, can also be used.

In some embodiments, at least one of Ar$^5$ has at least one substituent. Substituent groups can be present in order to alter the physical or electronic properties of the host material. In some embodiments, the substituents improve the processability of the host material. In some embodiments, the substituents increase the solubility and/or increase the Tg of the host material. In some embodiments, the substituents are selected from the group consisting of D, alkyl groups, alkoxy groups, silyl groups, siloxane, and combinations thereof.

In some embodiments, Q is an aryl group having at least two fused rings. In some embodiments, Q has 3-5 fused aromatic rings. In some embodiments, Q is selected from the group consisting of chrysene, phenanthrene, triphenylene, phenanthroline, naphthalene, anthracene, quinoline and isoquinoline.

The dopant is an electroactive material which is capable of electroluminescence having an emission maximum between 380 and 750 nm. In some embodiments, the dopant emits red, green, or blue light.

Electroluminescent ("EL") materials which can be used as a dopant in the electroactive layer, include, but are not limited to, small molecule organic luminescent compounds, luminescent metal complexes, conjugated polymers, and mixtures thereof. Examples of small molecule luminescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds. Examples of conjugated polymers include, but are not limited to poly(phenylenevinylenes), polyfluorenes, poly(spirobifluorenes), polythiophenes, poly (p-phenylenes), copolymers thereof, and mixtures thereof.

Examples of red light-emitting materials include, but are not limited to, periflanthenes, fluoranthenes, and perylenes. Red light-emitting materials have been disclosed in, for example, U.S. Pat. No. 6,875,524, and published US application 2005-0158577.

Examples of green light-emitting materials include, but are not limited to, diaminoanthracenes, and polyphenylenevinylene polymers. Green light-emitting materials have been disclosed in, for example, published PCT application WO 2007/021117.

Examples of blue light-emitting materials include, but are not limited to, diarylanthracenes, diaminochrysenes, diaminopyrenes, and polyfluorene polymers. Blue light-emitting materials have been disclosed in, for example, U.S. Pat. No. 6,875,524, and published US applications 2007-0292713 and 2007-0063638.

In some embodiments, the dopant is an organic compound. In some embodiments, the dopant is selected from the group consisting of a non-polymeric spirobifluorene compound and a fluoranthene compound.

In some embodiments, the dopant is a compound having aryl amine groups. In some embodiments, the electroactive dopant is selected from the formulae below:

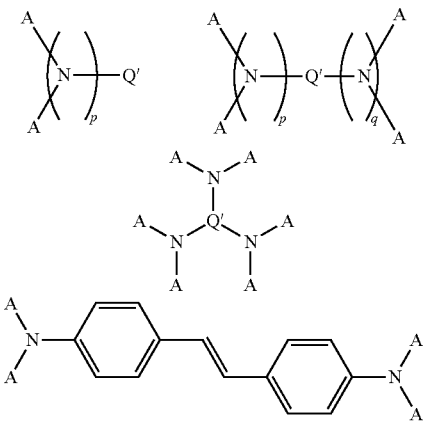

where:

A is the same or different at each occurrence and is an aromatic group having from 3-60 carbon atoms;

Q' is a single bond or an aromatic group having from 3-60 carbon atoms;

p and q are independently an integer from 1-6.

In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the dopant has the formula below:

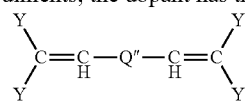

where:

Y is the same or different at each occurrence and is an aromatic group having 3-60 carbon atoms;

Q" is an aromatic group, a divalent triphenylamine residue group, or a single bond.

In some embodiments, the dopant is an aryl acene. In some embodiments, the dopant is a non-symmetrical aryl acene.

In some embodiments, the dopant is an anthracene derivative having Formula V:

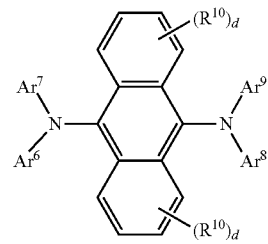

Formula V wherein:

$R^{10}$ is the same or different at each occurrence and is selected from the group consisting of D, alkyl, alkoxy and aryl, where adjacent $R^{10}$ groups may be joined together to form a 5- or 6-membered aliphatic ring;

$Ar^6$ through $Ar^9$ are the same or different and are selected from the group consisting of aryl groups;

d is the same or different at each occurrence and is an integer from 0 to 4; and In some embodiments, the dopant of Formula V is deuterated. In some embodiments, the aryl groups are deuterated. In some embodiments, the alkyl groups are deuterated. In some embodiments, the dopant is at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, the dopant is a chrysene derivative having Formula VI:

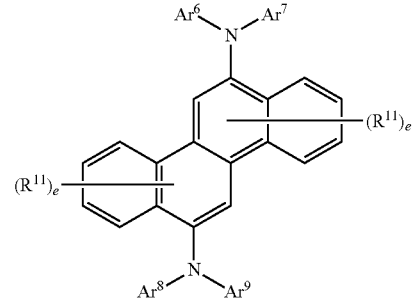

Formula VI wherein:

$R^{11}$ is the same or different at each occurrence and is selected from the group consisting of D, alkyl, alkoxy aryl, fluoro, cyano, nitro, —$SO_2R^{12}$, where $R^{12}$ is alkyl or perfluoroalkyl, where adjacent $R^{11}$ groups may be joined together to form a 5- or 6-membered aliphatic ring;

$Ar^6$ through $Ar^9$ are the same or different and are selected from the group consisting of aryl groups; and e is the same or different at each occurrence and is an integer from 0 to 5

In some embodiments, the dopant of Formula VI is deuterated. In some embodiments, the aryl groups are deuterated. In some embodiments, the alkyl groups are deuterated. In some embodiments, the dopant is at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

Some non-limiting examples of green dopants are compounds D1 through D8 shown below.

D1:

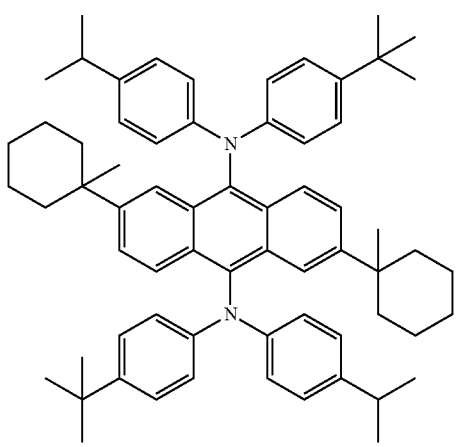

D2:

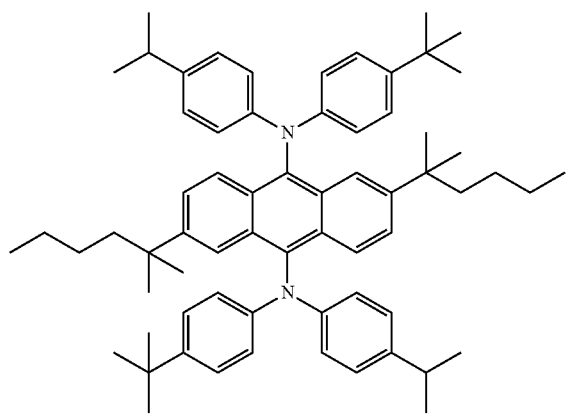

D3:

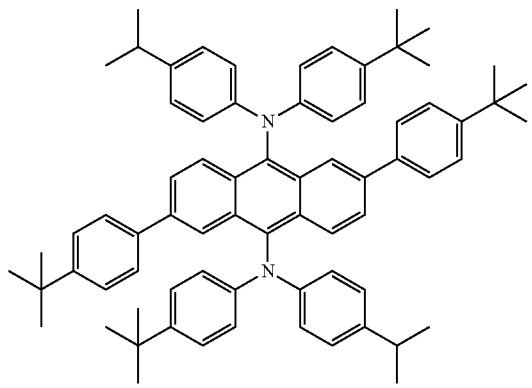

D4:

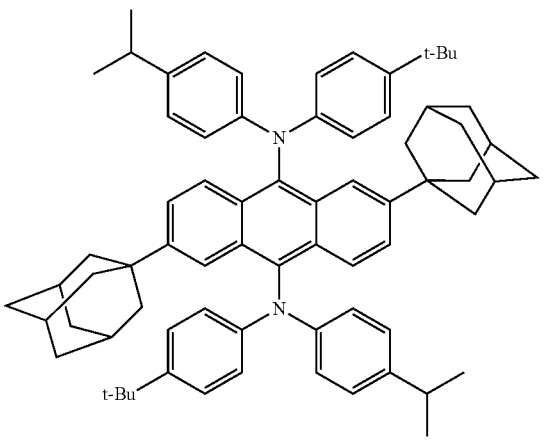

D5:

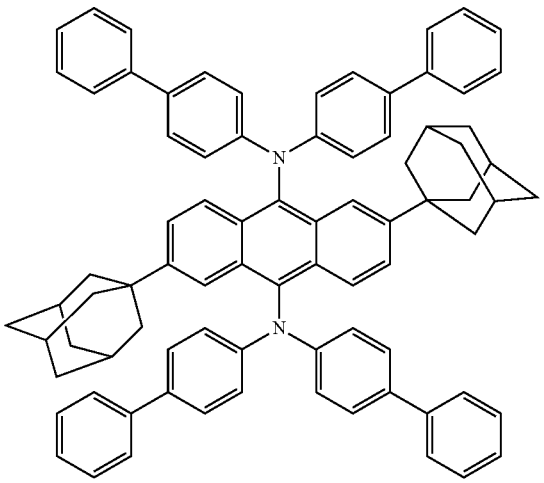

D6:
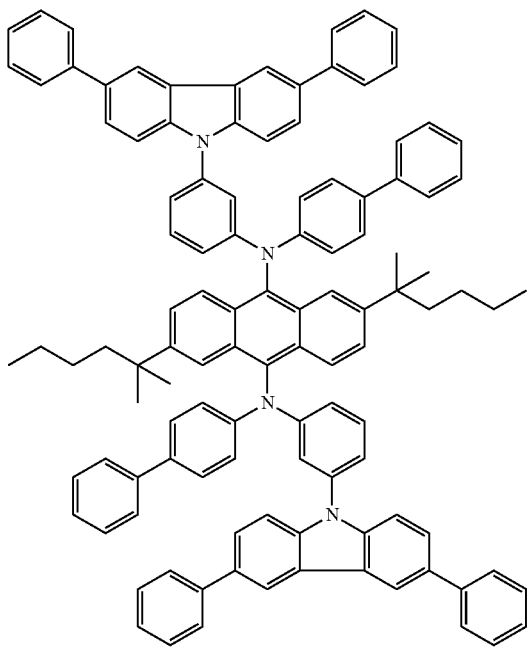
D7:
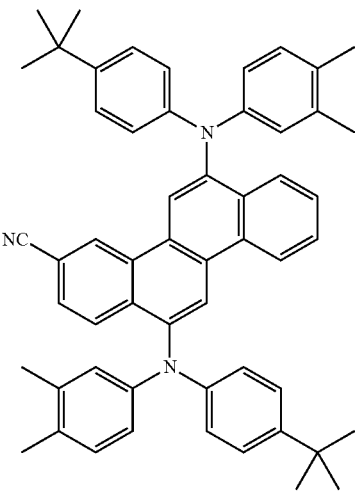
D8:
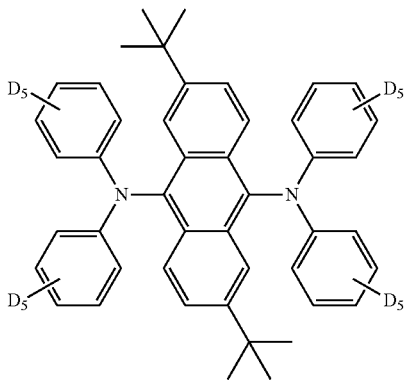
Some non-limiting examples of blue dopants are compounds D9 through D16 shown below.
D9:
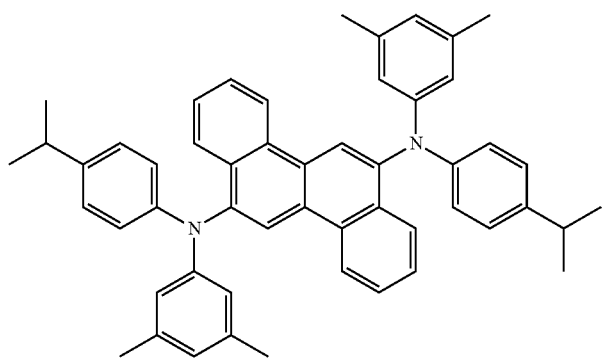

D10:
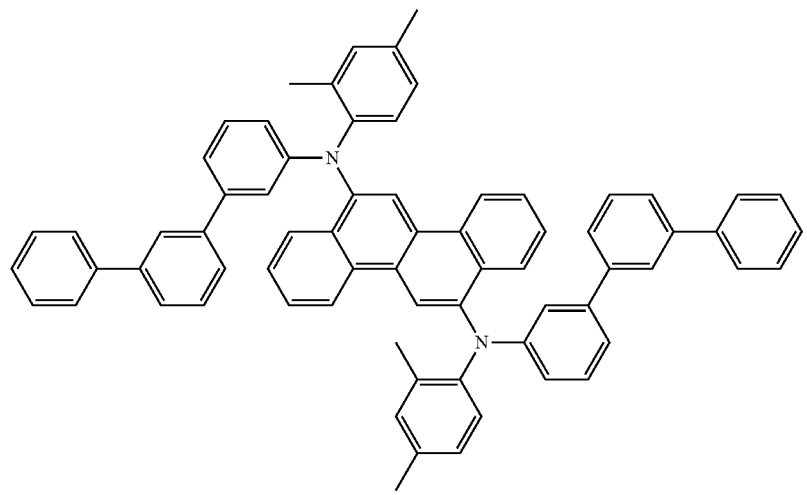
D11:
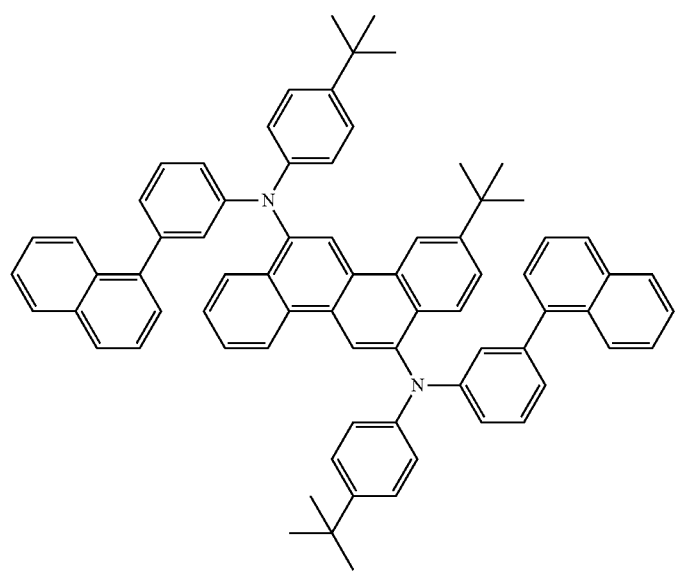
D12:
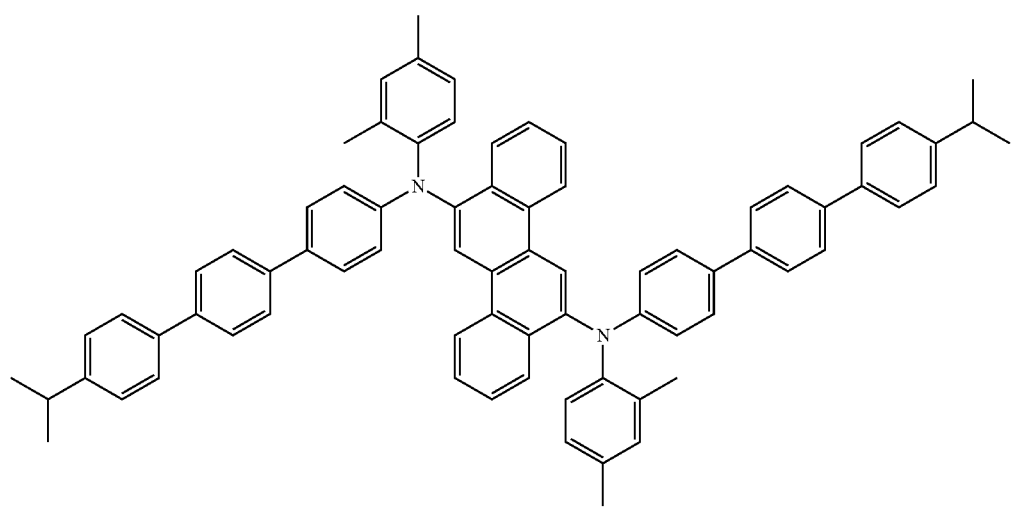

D13:
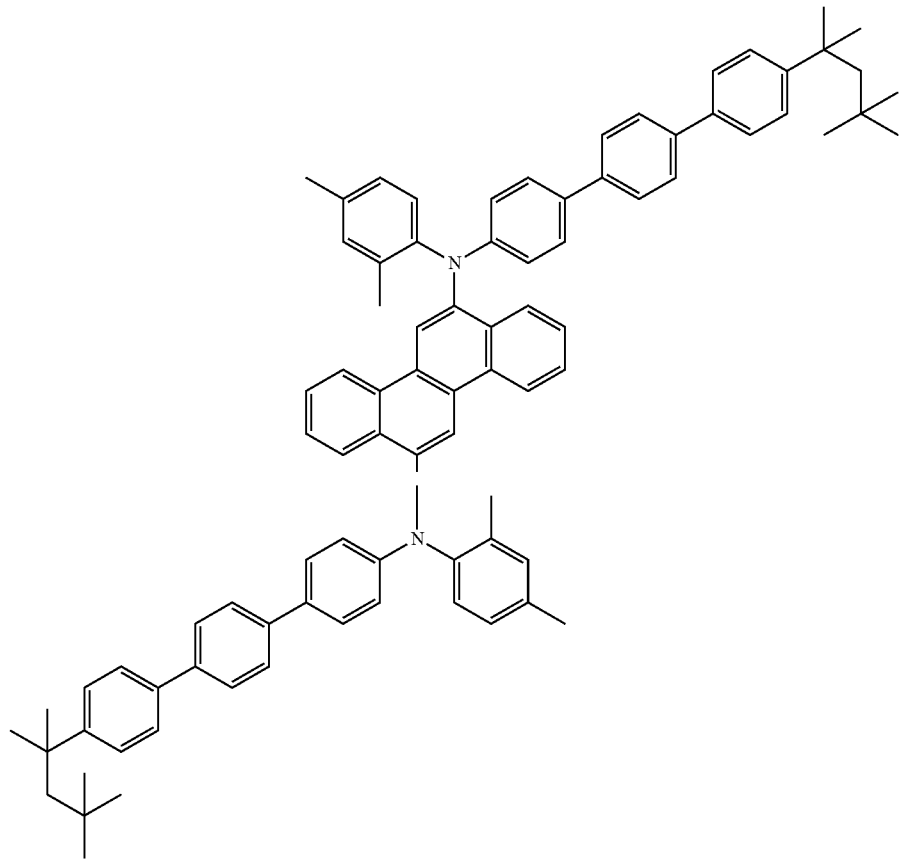
D14:
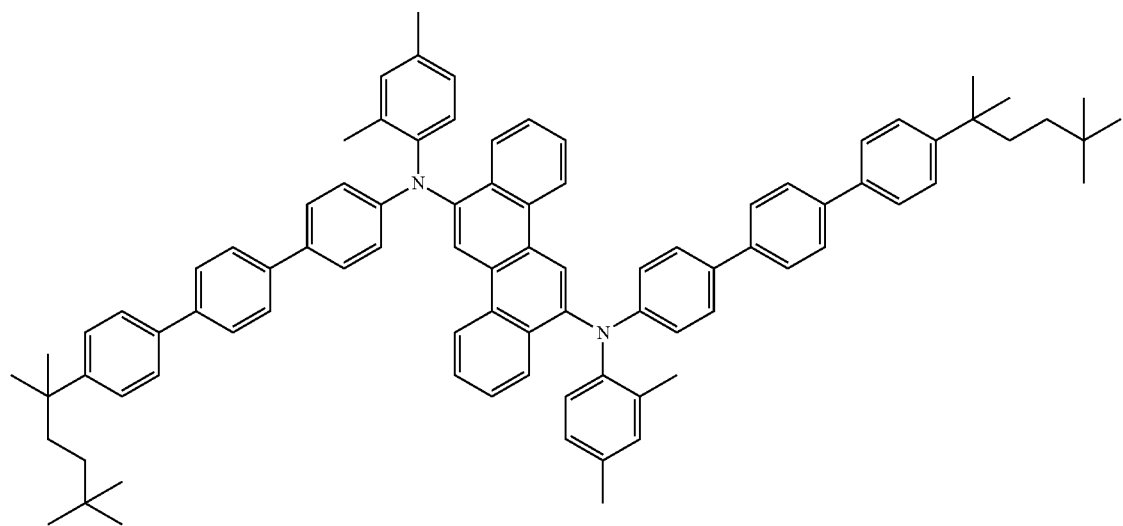

D15:

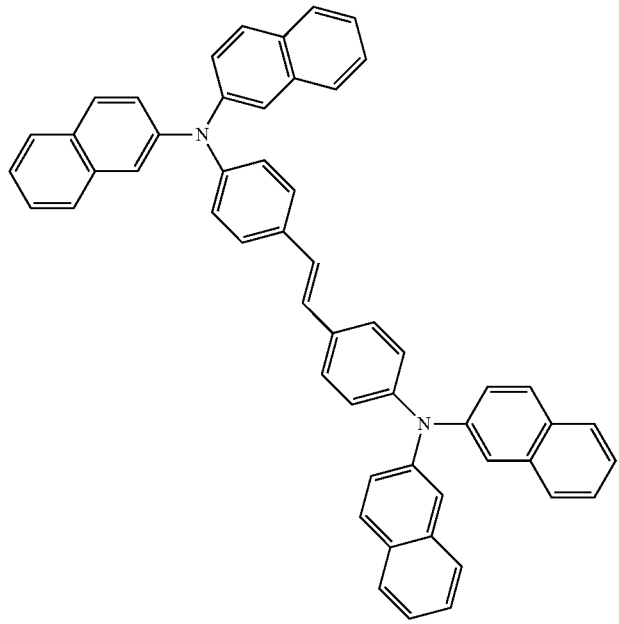

D16:

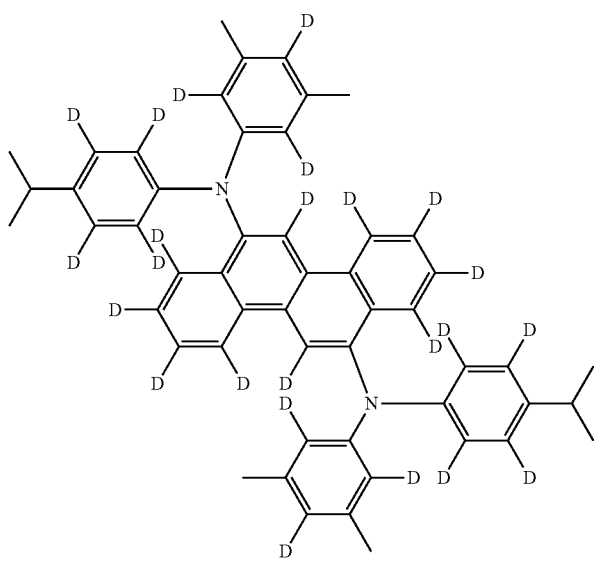 [SMILES: [2H]c1c(C)c([2H])c(N(c2c([2H])c([2H])c(C(C)C)c([2H])c2[2H])c2c([2H])c3c4c([2H])c([2H])c([2H])c([2H])c4c(N(c4c([2H])c([2H])c(C(C)C)c([2H])c4[2H])c4c([2H])c(C)c([2H])c(C)c4[2H])c([2H])c3c3c([2H])c([2H])c([2H])c([2H])c23)c([2H])c1C]

In some embodiments, the electroactive dopant is selected from the group consisting of amino-substituted chrysenes and amino-substituted anthracenes.

In some embodiments, the new deuterated compound described herein is an electroluminescent material and is present as an electroactive material.

b. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," Nature vol. 357, pp 477-479 (11 Jun. 1992). At least one of the anode and cathode is desirably at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules.

They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. Such materials have been described in, for example, published U.S. patent applications 2004-0102577, 2004-0127637, and 2005/205860

In some embodiments, the hole transport layer 130 comprises the new deuterated compound of Formula I. Examples of other hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (—NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

In some embodiments, the electron transport layer 150 comprises the new deuterated compound of Formula I. Examples of other electron transport materials which can be used in layer 150 include metal chelated oxinoid compounds, such as tris(8-hydroxyquinolato)aluminum (Alq$_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. The electron-transport layer may also be doped with n-dopants, such as Cs or other alkali metals. Layer 150 can function both to facilitate electron transport, and also serve as a buffer layer or confinement layer to prevent quenching of the exciton at layer interfaces. Preferably, this layer promotes electron mobility and reduces exciton quenching.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and Li$_2$O can also be deposited between the organic layer and the cathode layer to lower the operating voltage.

It is known to have other layers in organic electronic devices. For example, there can be a layer (not shown) between the anode 110 and hole injection layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

The present invention also relates to an electronic device comprising at least one active layer positioned between two electrical contact layers, wherein the at least one active layer of the device includes the anthracene compound of Formula 1. Devices frequently have additional hole transport and electron transport layers.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the anthracene compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The compounds of the invention often are photoluminescent and can be useful in applications other than OLEDs, such as oxygen sensitive indicators and as luminescent indicators in bioassays.

EXAMPLES

The following examples illustrate certain features and advantages of the present invention. They are intended to be illustrative of the invention, but not limiting. All percentages are by weight, unless otherwise indicated.

Synthesis of Dopant Materials (1) Dopant D6 was Prepared as Follows

Synthesis of Intermediate (a)

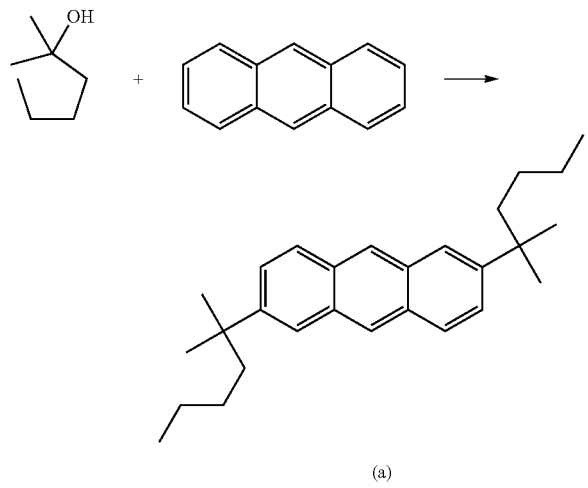

(a)

35 g (300 mM) 2-methyl-2-hexanol and 17.8 g anthracene (100 mM) were added to 50 mL trifluoroacetic acid and refluxed under nitrogen for overnight. Solution quickly darkened to a brown heterogeneous material. This was cooled to room temp., evaporated under a nitrogen stream and extracted into methylene chloride. Separated and dried organic layer over magnesium sulfate and evaporated to dryness. Extracted the resulting solid through a silica column with hexanes and recovered pale yellow solution. Evaporated to a thick yellow oil and recrystallized from acetone/methanol by slow cooling and recrystallization from methanol. NMR analysis confirmed the structure.

Synthesis of Intermediate (b)

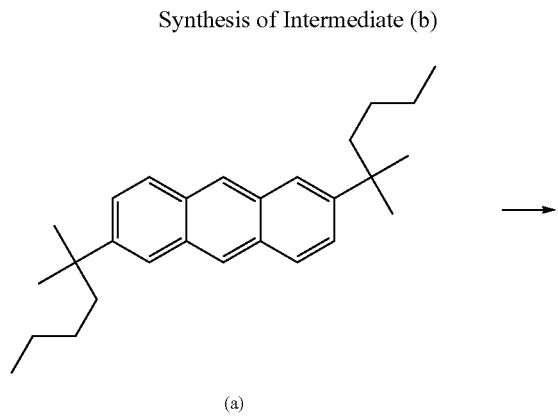

(a)

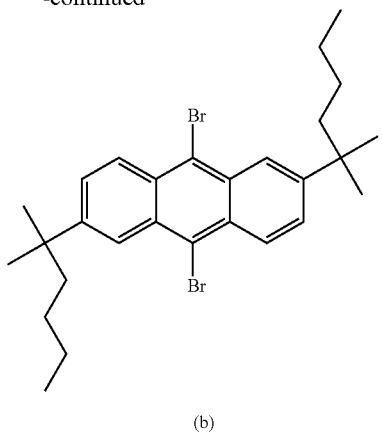

(b)

6.0 g (16 mM) intermediate (a) (pure 2,6 isomer) was taken into 100 mL dichloroethane and 2.10 mL bromine (40 mM) was added dropwise with stirring at room temperature for 4 hrs. This was poured into water and sodium sulfite was added to consume remaining bromine. This was then extracted into methylene chloride and the organic layer dried over magnesium sulfate. The resulting material was passed through alumina column with methylene chloride eluent and then evaporated and methanol added to precipitate a pale yellow solid. Yield ~7.2 g Synthesis of Intermediate (c)

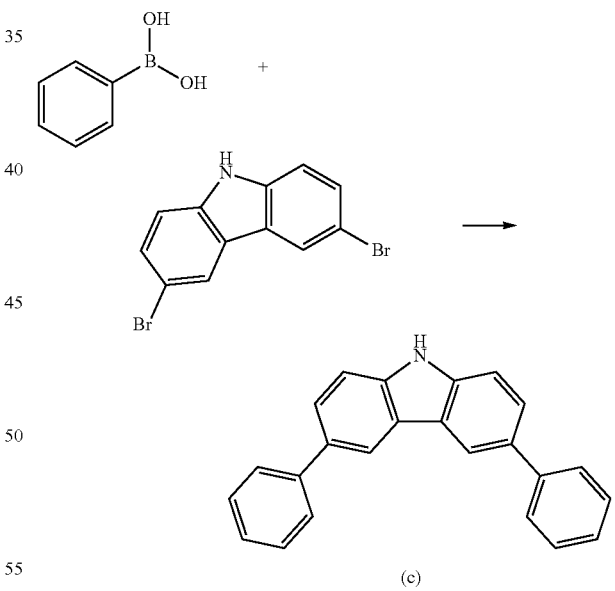

(c)

To 25 g of the bromo-carbazole (77.7 mM) in glove box was added 18.9 g (155 mM) boronic acid. To this was added 1.0 g Pd2DBA3 (1.0 mM), 0.5 g P(t-Bu)3 (2.1 mM) and 20 g sodium carbonate (200 mM) and all was dissolved into 200 mL dioxane with 50 mL water. This was mixed and heated in a glove box in mantle at 50° C. for 1 hr then warmed gently (minimum rheostat setting) under nitrogen overnight. The solution immediately was dark purple and on reaching ~500 it was dark brown. Added water to brown solution outside glove box and it separated an oily yellow layer. Added DCM and separated organic layer. Filtrate was dried over magnesium sulfate to give a light orange solution which generated white solid on evaporation. After evaporation to low volume and addition of hexanes, the white solid was filtered off. The solid was washed well with methanol until washings were colorless, and then rinsed with ether and suctioned dry to give 21 g white solid. The structure was confirmed by NMR analysis.

Synthesis of Intermediate (d)

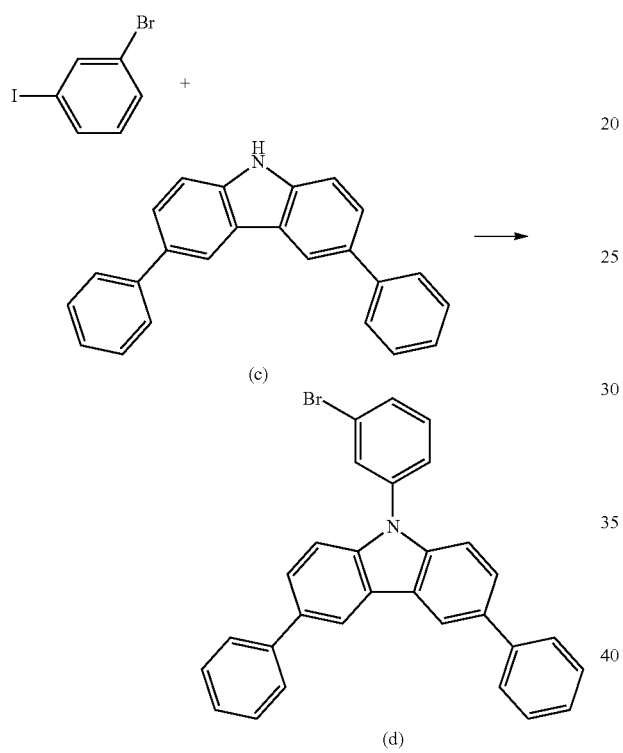

0.4 g Pd2DBA3, 0.4 g 1,1'-bis(diphenylphosphine)ferrocene (DPPF) and 4.3 g sodium t-butoxide were mixed together and dissolved into 200 mL xylenes in glove box. Stirred 15 mins then added 25 g of 3-iodo-bromobenzene. Stirred 15 mins then added 10 g carbazole and the mix was brought to reflux. Refluxed o/n. using an air condensor. Solution immediately was dark purple/brown but on reaching ~800 it was dark reddish brown and cloudy. After heating close to reflux overnight, the solution was dark brown and clear. Evaporated outside the glove box in nitrogen stream and then dissolved in DCM and extracted (soxhlet) through a bed of silica and basic alumina (stacked in soxhlet) using DCM/hexanes. Collected dark orange solution and evaporated to dryness. A dark orange oil remained. This was washed with methanol and then dissolve into ether and reprecipitated with methanol. The orange brown oil was evaporated to low volume in ether and then acetone/methanol was added to precipitate an off-white solid in yield of ~6.4 g. This was collected by filtration, washed with a little acetone and suctioned dry. The structure was confirmed by NMR analysis.

Synthesis of Intermediate (e)

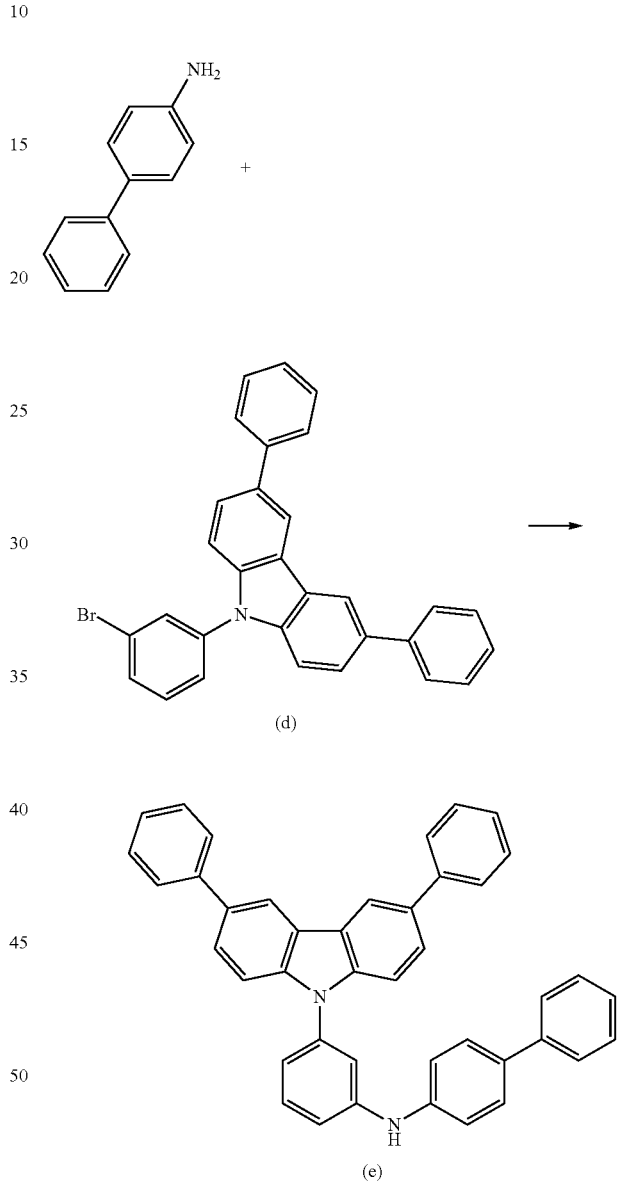

To 4.8 g of intermediate (d) (0.01 M) in glove box was added 1.7 g amine (0.01 M). To this was added 0.10 g Pd2DBA3 (0.11 mM), 0.045 g P(t-Bu)3 (0.22 mM) and 1.1 g t-BuONa and all were dissolved into 25 mL toluene. Upon addition of catalyst materials, there was a mild exotherm. This was heated in glove box in mantle at 80° C. under nitrogen for 2 hr as a dark brown solution (thick). After cooling, the solution was worked up by β-alumina chromatography eluting with DCM. A dark yellow solution with bright purple/blue photoluminescence was collected. This was evaporated in nitrogen to low volume to form a viscous orange oil, which on cooling solidified to a dark yellow glass. This was stirred into methanol/DCM and allowed to crystallize as a pale yellow/white solid in ~5 g yield. The structure was confirmed by NMR analysis.

Synthesis of Dopant D6:

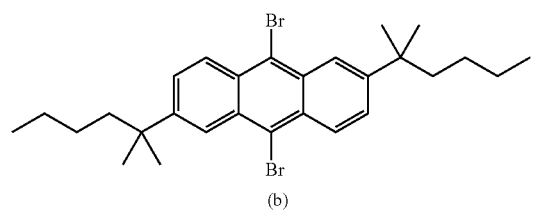

(b)

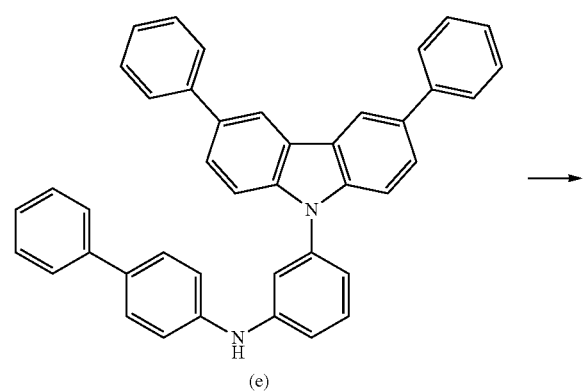

(e)

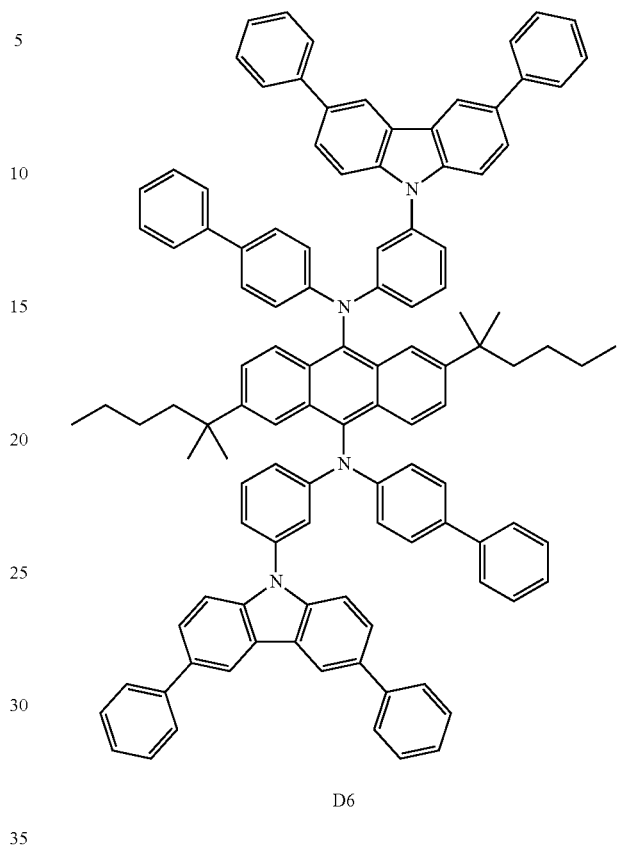

D6

To 1.32 g of intermediate (b) (2.5 mM) in glove box was added 2.81 g (5 mM) intermediate (e) and 0.5 g t-BuONa (5 mM) with 50 mL toluene. To this was added 0.2 g Pd2DBA3 (0.2 mM), 0.08 g P(t-Bu)3 (0.4 mM) dissolved in 10 mL toluene. After mixing, the solution slowly exothermed and became yellow brown. This was mixed and heated in glove box in mantle at ~100° C. under nitrogen for 1 hr. Solution immediately was dark purple but on reaching ~80° C. it was dark yellow green with noticeable green luminescence. Stirred overnight at lowest rheostat setting. After cooling, the material was removed from glove box and filtered through an acidic-alumina plug eluting with toluene and methylene chloride. The dark orange solution was evaporated to low volume. This was passed through a silica column (using 60:40 toluene: hexanes). A yellow orange solution was collected which showed blue leading spots on TLC. This was redissolved in hexanes:toluene (80:20) and passed n through acidic alumina eluting with 80% hexanes/toluene. The faster running blue bands (anthracene and monaminated anthracene) were discarded. The resulting yellow band was evaporated to low volume and crystallized from toluene/acetone/methanol. This was washed with methanol and hexanes and suctioned dry to obtain a free flowing microcrystalline yellow powder. The structure was confirmed by NMR analysis.

(2) Dopant D12, N6,N12-bis(2,4-dimethylphenyl)-N6,N12-bis(4"-isopropylterphenyl-4-yl)chrysene-6,12-diamine, was Prepared as Follows

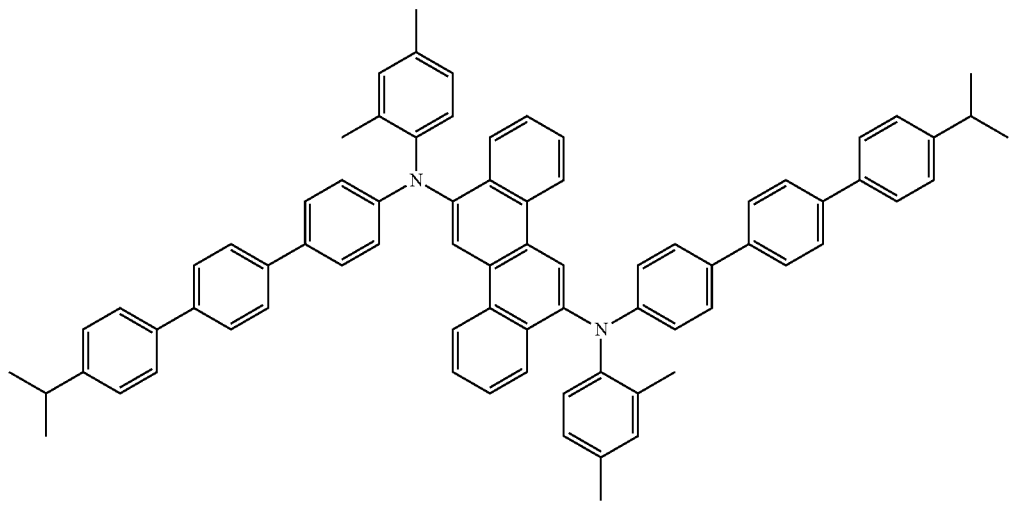 [SMILES: Cc1ccc(N(c2ccc(-c3ccc(-c4ccc(C(C)C)cc4)cc3)cc2)c2cc3c4ccccc4c(N(c4ccc(-c5ccc(-c6ccc(C(C)C)cc6)cc5)cc4)c4ccc(C)cc4C)cc3c3ccccc23)c(C)c1]

In a drybox, 6,12-dibromochrysene (0.54 g, 1.38 mmol), N-(2,4-dimethylphenyl)-N-(4'-isopropylterphenyl-4-yl) amine (1.11 g, 2.82 mmol), tris(tert-butyl)phosphine (0.028 g, 0.14 mmol) and tris(dibenzylideneacetone) dipalladium(0) (0.063 g, 0.069 mmol) were combined in round bottom flask and dissolved in 20 ml of dry toluene. The solution was stirred for a minute and followed by sodium tert-butoxide (0.29 g, 3.03 mmol) and 10 ml of dry toluene. A heating mantle was added and the reaction heated to 60 C for 3 days. The reaction mixture was then cooled to room temperature and filtered through a 1 inch plug of silica gel and one inch of Celite, washing with toluene (500 mL). Removal of volatiles under reduced pressure gave a yellow solid. The crude product was purified further by silica gel column chromatography using a gradient of chloroform in hexanes (0% to 40%). Recrystallization from DCM and acetonitrile yielded 0.540 g (40%) of product as a yellow solid. $^1$H NMR (CDCl$_3$) is consistent with structure.

(3) Dopant D13, N6,N12-bis(2,4-dimethylphenyl)-N6,N12-bis(4"-tert-octylterphenyl-4-yl)chrysene-6,12-diamine, was Made Using a Procedure Analogous to the Synthesis of D12
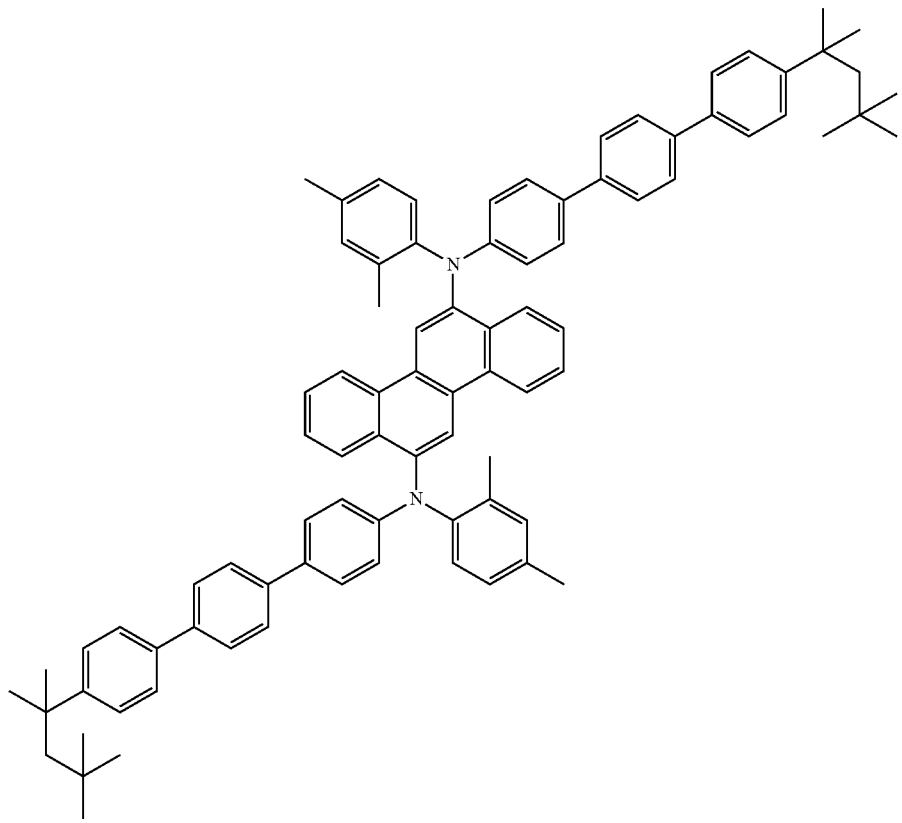 [SMILES: Cc1ccc(N(c2ccc(-c3ccc(-c4ccc(C(C)(C)CC(C)(C)C)cc4)cc3)cc2)c2cc3c4ccccc4c(N(c4ccc(-c5ccc(-c6ccc(C(C)(C)CC(C)(C)C)cc6)cc5)cc4)c4ccc(C)cc4C)cc3c3ccccc23)c(C)c1]
Comparative Example A
This example illustrates the preparation of a non-deuterated compound, Comparative Compound A.
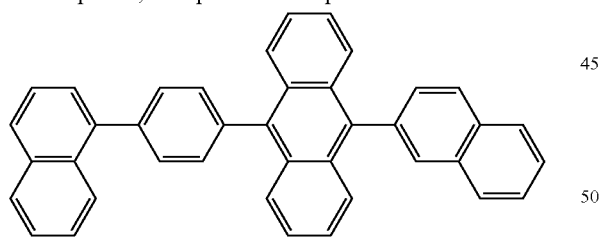
This compound can be prepared according to the following scheme:
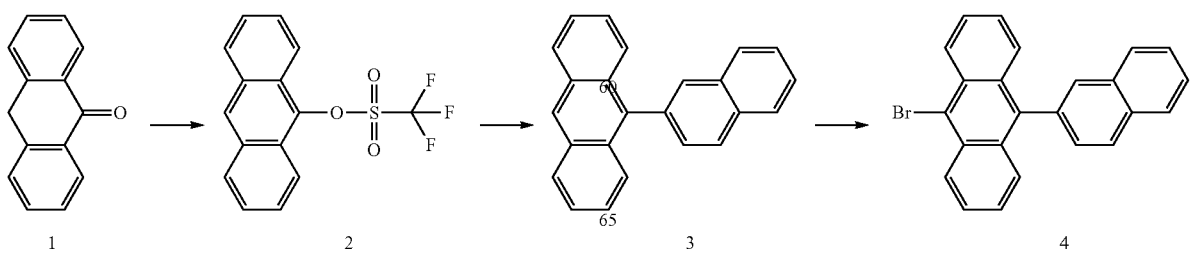
1      2      3      4

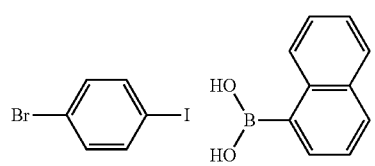
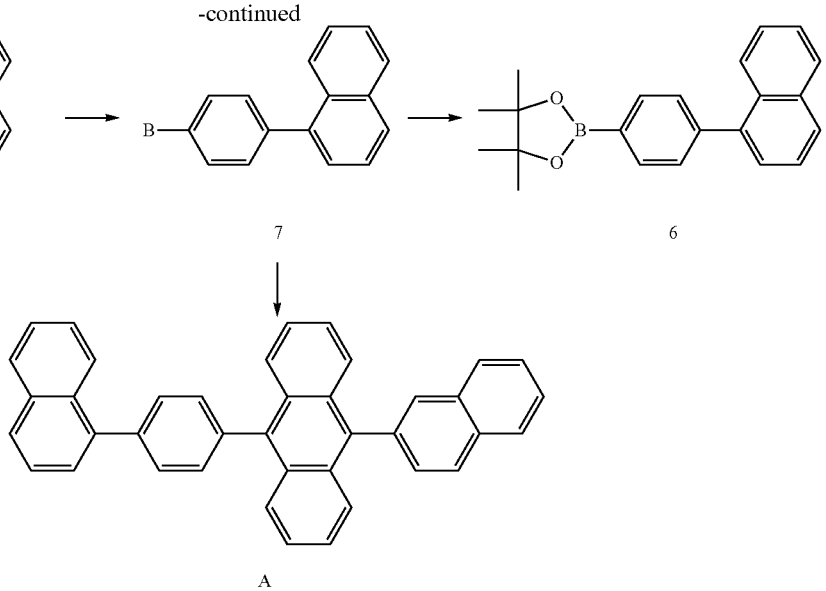

Synthesis of Compound 2:

In a 3 L flask fitted with a mechanical stirrer, dropping funnel, thermometer and $N_2$ bubbler was added anthrone, 54 g (275.2 mmol) in 1.5 L dry methylene chloride. The flask was cooled in an ice bath and 1,8-diazabicyclo[5.4.0]undec-7-ene ("DBU"), 83.7 ml (559.7 mmol) was added by dropping funnel over 1.5 hr. The solution turned orange, became opaque, then turned deep red. To the still cooled solution was added triflic anhydride, 58 ml (345.0 mmol) via syringe over about 1.5 hr keeping the temperature of the solution below 5° C. The reaction was allowed to proceed for 3 hr at room temperature, after which 1 mL additional triflic anhydride was added and stirring at RT continued for 30 min. 500 mL water was added slowly and the layers separated. The aqueous layer was extracted with 3×200 mL dichloromethane ("DCM") and the combined organics dried over magnesium sulfate, filtered and concentrated by rotary evaporation to give a red oil. Column chromatography on silica gel followed by crystallization from hexanes afforded 43.1 g (43%) of a tan powder Synthesis of Compound 3:

To a 200 mL Kjeldahl reaction flask equipped with a magnetic stirring bar in a nitrogen-filled glove box were added anthracen-9-yl trifluoromethanesulfonate (6.0 g, 18.40 mmol), Napthalen-2-yl-boronic acid (3.78 g 22.1 mmol), potassium phosphate tribasic (17.50 g, 82.0 mmol), palladium(II) acetate (0.41 g, 1.8 mmol), tricyclohexylphosphine (0.52 g, 1.8 mmol) and THF (100 mL). After removal from the dry box, the reaction mixture was purged with nitrogen and degassed water (50 mL) was added by syringe. A condenser was then added and the reaction was refluxed overnight. The reaction was monitored by TLC. Upon completion the reaction mixture was cooled to room temperature. The organic layer was separated and the aqueous layer was extracted with DCM. The organic fractions were combined, washed with brine and dried with magnesium sulfate. The solvent was removed under reduced pressure. The resulting solid was washed with acetone and hexane and filtered. Purification by column chromatography on silica gel afforded 4.03 g (72%) of product as pale yellow crystalline material.

Synthesis of Compound 4:

9-(naphthalen-2-yl)anthracene, 11.17 g (36.7 mmol) was suspended in 100 mL DCM. N-bromosuccinimide 6.86 g (38.5 mmol) was added and the mixture stirred with illumination from a 100W lamp. A yellow clear solution formed and then precipitation occurred. The reaction was monitored by TLC. After 1.5 h, the reaction mixture was partially concentrated to remove methylene chloride, and then crystallized from acetonitrile to afford 12.2 g of pale yellow crystals (87%).

Synthesis of Compound 7:

To a 500 mL round bottom flask equipped with a stir bar in a nitrogen-filled glove box were added naphthalen-1-yl-1-boronic (14.2 g, 82.6 mmol), acid, 1-bromo-2-iodobenzene (25.8 g, 91.2 mmol), tetrakis(triphenylphospine) palladium (0) (1.2 g, 1.4 mmol), sodium carbonate (25.4 g, 240 mmol), and toluene (120 mL). After removal from the dry box, the reaction mixture was purged with nitrogen and degassed water (120 mL) was added by syringe. The reaction flask was then fitted with a condenser and the reaction was refluxed for 15 hours. The reaction was monitored by TLC. The reaction mixture was cooled to room temperature. The organic layer was separated and the aqueous layer was extracted with DCM. The organic fractions were combined and the solvent was removed under reduced pressure to give a yellow oil. Purification by column chromatography using silica gel afforded 13.6 g of a clear oil (58%).

Synthesis of Compound 6:

To a 1-liter flask equipped with a magnetic stirring bar, a reflux condenser that was connected to a nitrogen line and an oil bath, were added 4-bromophenyl-1-naphthalene (28.4 g, 10.0 mmol), bis(pinacolate) diboron (40.8 g, 16.0 mmol), $Pd(dppf)_2Cl_2$ (1.64 g, 2.0 mmol), potassium acetate (19.7 g, 200 mmol), and DMSO (350 mL). The mixture was bubbled with nitrogen for 15 min and then $Pd(dppf)_2Cl_2$ (1.64 g, 0.002 mol) was added. During the process the mixture turned to a dark brown color gradually. The reaction was stirred at 120° C. (oil bath) under nitrogen for 18 h. After cooling the mixture was poured into ice water and extracted with chloroform (3×). The organic layer was washed with water (3×) and saturated brine (1×) and dried with MgSO4. After filtration and removal of solvent, the residue was purified by chromatography on a silica gel column. The product containing fractions were combined and the solvent was removed by rotary evaporation. The resulting white solid was crystallized from hexane/chloroform and dried in a vacuum oven at 40° C. to give the product as white crystalline flakes (15.0 g in 45% yield). 1H and 13C-NMR spectra are in consistent with the expected structure.

Synthesis of Comparative Compound A

To a 250 mL flask in glove box were added (2.00 g, 5.23 mmol), 4,4,5,5-tetramethyl-2-(4-(naphthalen-4-yl)phenyl)-1,3,2-dioxaborolane (1.90 g, 5.74 mmol), tris(dibenzylideneacetone) dipalladium(0) (0.24 g, 0.26 mmol), and toluene (50 mL). The reaction flask was removed from the dry box and fitted with a condenser and nitrogen inlet. Degassed aqueous sodium carbonate (2 M, 20 mL) was added via syringe. The reaction was stirred and heated to 90° C. overnight. The reaction was monitored by HPLC. After cooling to room temperature, the organic layer was separated. The aqueous layer was washed twice with DCM and the combined organic layers were concentrated by rotary evaporation to afford a grey powder. Purification by filtration over neutral alumina, hexanes precipitation, and column chromatography over silica gel afforded 2.28 g of a white powder (86%).

The product was further purified as described in published U.S. patent application 2008-0138655, to achieve an HPLC purity of at least 99.9% and an impurity absorbance no greater than 0.01.

Figure 2:
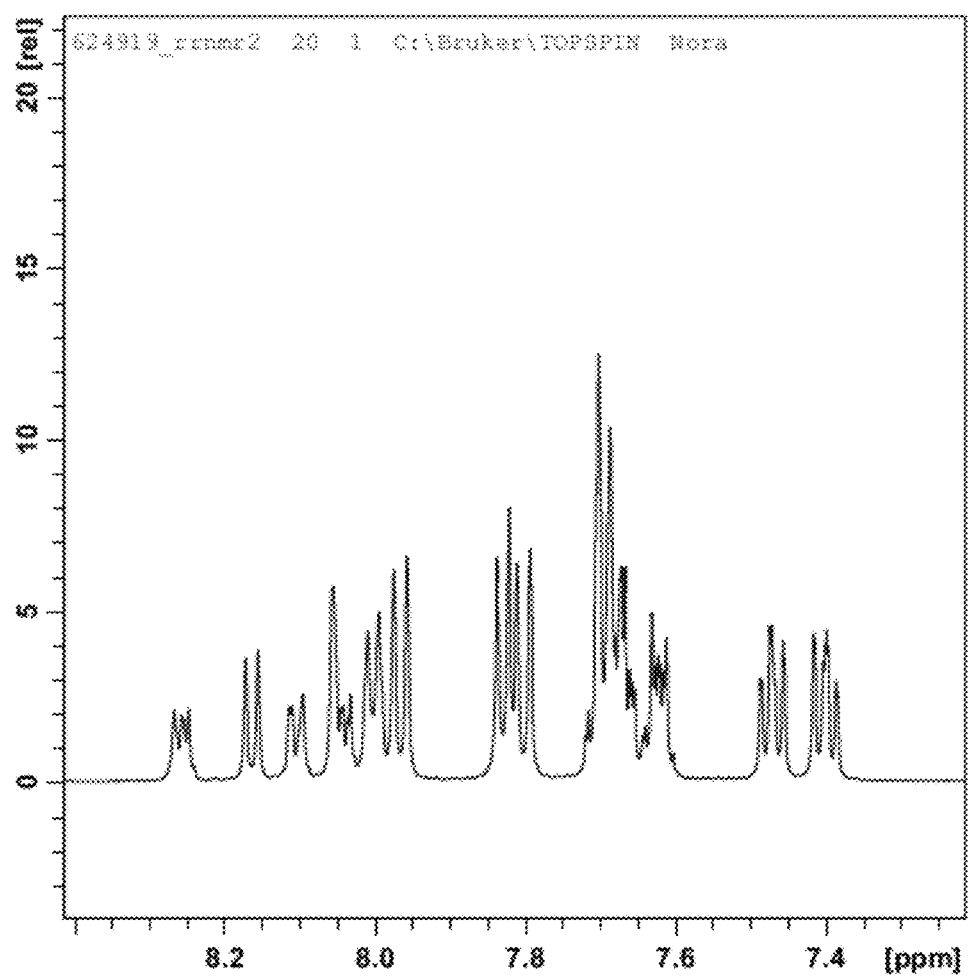
FIG. 2 includes the $^1$H NMR spectrum of the comparative compound of Comparative Example A.

The $^1$H NMR spectrum of Compound A is given in FIG. 2.

Example 1

This example illustrates the preparation of a compound having Formula I, Compound H14.

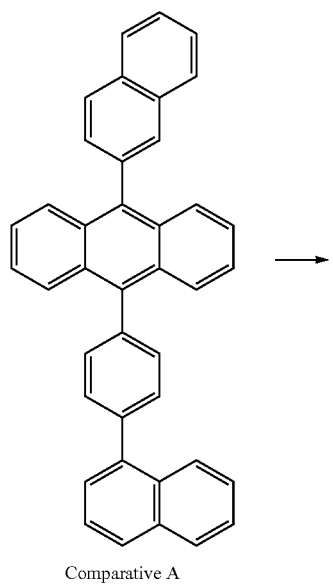

Comparative A

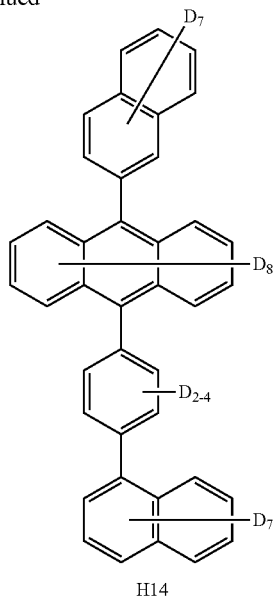

H14

Under an atmosphere of nitrogen, AlCl$_3$ (0.48 g, 3.6 mmol) was added to a perdeuterobenzene or benzene-D6 (C$_6$D$_6$) (100 mL) solution of comparative compound A from Comparative Example A (5 g, 9.87 mmol). The resulting mixture was stirred at room temperature for six hours after which D$_2$O (50 mL) was added. The layers were separated followed by washing the water layer with CH$_2$Cl$_2$ (2×30 mL). The combined organic layers were dried over magnesium sulfate and the volatiles were removed by rotary evaporation. The crude product was purified via column chromatography. The deuterated product H1 (x+y+n+m=21-23) was obtained (4.5 g) as a white powder.

The product was further purified as described in published U.S. patent application 2008-0138655, to achieve an HPLC purity of at least 99.9% and an impurity absorbance no greater than 0.01. The material was determined to have the same level of purity as comparative compound A, from above.

Figure 3:
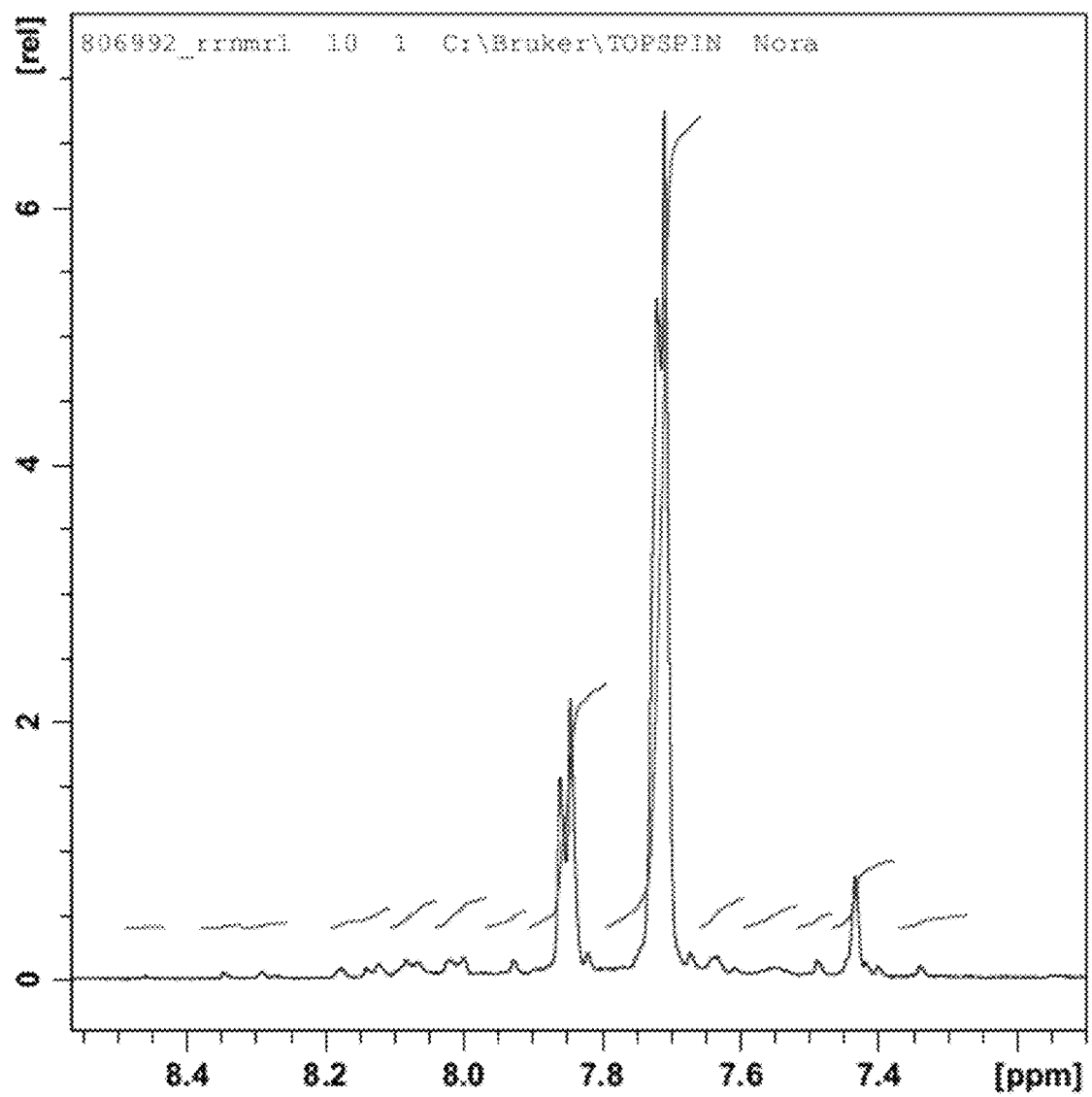
FIG. 3 includes the $^1$H NMR spectrum of the deuterated compound of Example 1.
Figure 4:
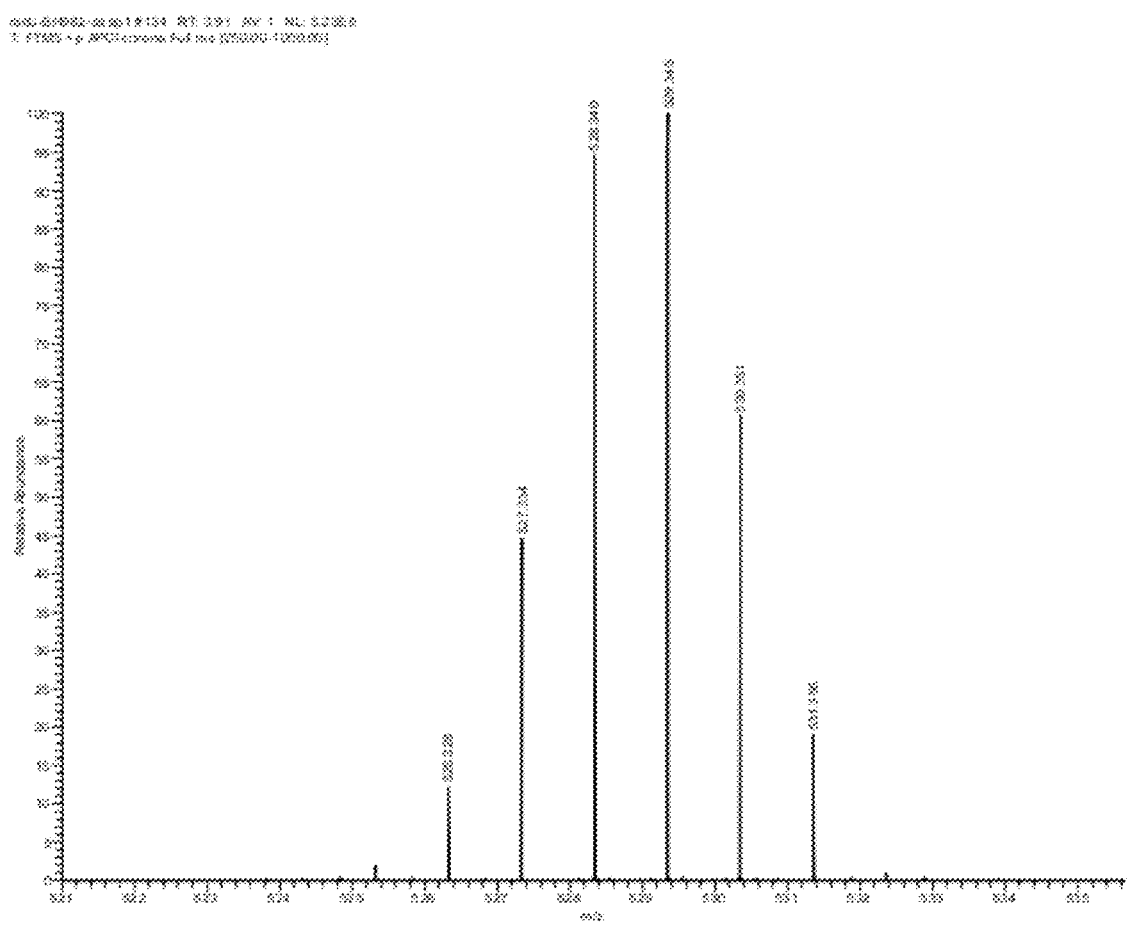
FIG. 4 includes the mass spectrum of the deuterated compound of Example 1.

The $^1$H NMR (CD$_2$Cl$_2$) and ASAP-MS are shown in FIGS. 3 and 4, respectively. The compound had the structure given below:

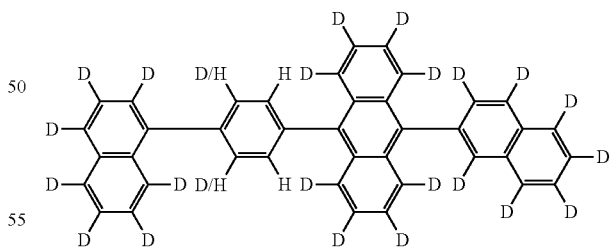

where "D/H" indicates approximately equal probability of H or D at this atomic position. The structure was confirmed by $^1$H NMR, $^{13}$H NMR, $^2$D NMR and $^1$H-$^{13}$C HSQC (Heteronuclear Single Quantum Coherence).

Examples 2 and 3 and Comparative Examples B and C

These examples demonstrate the fabrication and performance of a device with a blue emitter.

The device had the following structure on a glass substrate:
anode=Indium Tin Oxide (ITO): 50 nm hole injection layer=HIJ1 (50 nm), which is an aqueous dispersion of an electrically conductive polymer and a polymeric fluorinated sulfonic acid. Such materials have been described in, for example, published U.S. patent applications US 2004/0102577, US 2004/0127637, US 2005/0205860, and published PCT application WO 2009/018009.

hole transport layer=polymer P1, which is a non-crosslinked arylamine polymer (20 nm)

electroactive layer=13:1 host:dopant (40 nm), as shown in Table 1 electron transport layer=ET1, which is a metal quinolate derivative (10 nm)

cathode=CsF/Al (1.0/100 nm)

TABLE 1

Device Electroactive Layers

| Example | Host | Dopant |
|---|---|---|
| Comparative B-1 | Comp. Compound A | D12 |
| Comparative B-2 | Comp. Compound A | D12 |
| Comparative B-3 | Comp. Compound A | D12 |
| Comparative B-4 | Comp. Compound A | D12 |
| Ex. 2-1 | H14 | D12 |
| Ex. 2-2 | H14 | D12 |
| Ex. 2-3 | H14 | D12 |
| Ex. 2-4 | H14 | D12 |
| Comparative C-1 | Comp. Compound A | D13 |
| Comparative C-2 | Comp. Compound A | D13 |
| Ex. 3-1 | H14 | D13 |
| Ex. 3-2 | H14 | D13 |

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ1 was spin-coated over the ITO surface and heated to remove solvent. After cooling, the substrates were then spin-coated with a solution of a hole transport material, and then heated to remove solvent. After cooling the substrates were spin-coated with the emissive layer solution, and heated to remove solvent. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current needed to run the device. The unit is a cd/A. The power efficiency is the current efficiency multiplied by pi, divided by the operating voltage. The unit is lm/W. The device data is given in Table 2.

TABLE 2

Device Performance

| Ex. | CIE (x, y) | Voltage (V) | C.E. (cd/A) | E.Q.E. (%) | P.E. (lm/W) | Lifetest current density (mA/cm2) | Lifetest Luminance (nits) | Raw T50 (h) | Projected Lifetime T50 @1000 nits |
|---|---|---|---|---|---|---|---|---|---|
| Comp. B-1 | 0.135, 0.124 | 4.4 | 6.1 | 6.0 | 4.3 | 129 | 6837 | 410 | 10766 |
| Comp. B-2 | 0.135, 0.127 | 4.3 | 6.4 | 6.1 | 4.7 | 125 | 7002 | 410 | 11211 |
| Comp. B-3 | 0.136, 0.123 | 4.4 | 5.7 | 5.6 | 4.1 | 127 | 5906 | 430 | 8804 |
| Comp. B-4 | 0.134, 0.129 | 4.3 | 6.4 | 6.1 | 4.7 | 123 | 7021 | 430 | 11813 |
| Ex. 2-1 | 0.136, 0.119 | 4.4 | 5.7 | 5.7 | 4.1 | 136 | 7040 | 870 | 24010 |
| Ex. 2-2 | 0.137, 0.117 | 4.2 | 5.4 | 5.5 | 4.1 | 126 | 6244 | 830 | 18679 |
| Ex. 2-3 | 0.136, 0.118 | 4.2 | 5.7 | 5.7 | 4.2 | 129 | 6467 | 830 | 19828 |
| Ex. 2-4 | 0.136, 0.118 | 4.3 | 5.5 | 5.6 | 4.1 | 121 | 6148 | 870 | 19071 |
| Comp. C-1 | 0.135, 0.128 | 4.3 | 6.2 | 6.0 | 4.6 | 141 | 8018 | 490 | 16871 |
| Comp. C-2 | 0.135, 0.128 | 4.3 | 6.3 | 6.0 | 4.6 | 125 | 7136 | 510 | 14403 |
| Ex. 3-1 | 0.135, 0.122 | 4.3 | 6.0 | 5.9 | 4.4 | 121 | 6741 | 950 | 24356 |

TABLE 2-continued

| | | | | | Device Performance | | | |
|---|---|---|---|---|---|---|---|---|
| Ex. | CIE (x, y) | Voltage (V) | C.E. (cd/A) | E.Q.E. (%) | P.E. (lm/W) | Lifetest current density (mA/cm2) | Lifetest Luminance (nits) | Raw T50 (h) | Projected Lifetime T50 @1000 nits |
| Ex. 3-2 | 0.135, 0.124 | 4.2 | 6 | 5.8 | 4.4 | 126 | 6974 | 930 | 25257 |

\* All data @ 1000 nits,
CE = current efficiency;
CIEx and CIEy are the x and y color coordinates according to the C.I.E. chromaticity scale (Commission Internationale de L'Eclairage, 1931).
Raw T50 is the time in hours for a device to reach one-half the initial luminance at the lifetest luminance given.
Projected T50 is the projected lifetime at 1000 nits using an accelerator factor of 1.7.

It can be seen that with the deuterated host of the invention, the lifetime of devices is greatly increased, while maintaining other device properties. When emitter D12 was used, the comparative devices with a non-deuterated host (Comparative examples B-1 through B-4) had an average projected T50 of 10,649 hours. With the deuterated analog host H14 (Examples 2-1 through 2-4), the devices has an average projected T50 of 20,379 hours. When emitter D13 was used, the comparative devices (C-1 and C-2) had an average projected T50 of 15,637 hours. With the deuterated analog host H14 (3-1 and 3-2), the average projected T50 was 24,807 hours.

Example 4

This example illustrates the preparation of some deuterated intermediate compounds that can be used to synthesize compounds having Formula I with controlled levels of deuteration.

Intermediate 4A:

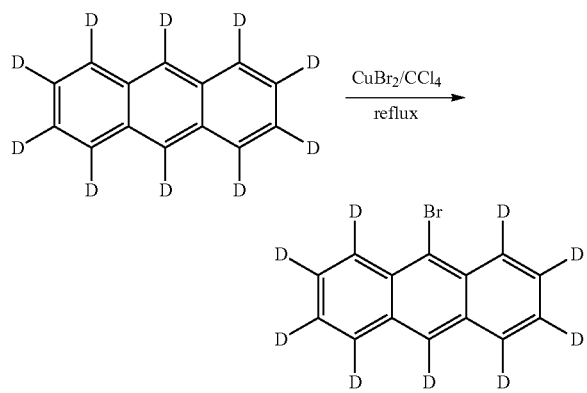

To a solution of anthracene-d10 (18.8 g, 0.10 mole) in 0014 (500 mL) was added anhydrous cupric bromide (45 g, 0.202 mole) in one portion. The reaction mixture was stirred and heated under reflux for 12 hours. The brown cupric chloride is gradually converted to white cuprous bromide, and hydrogen bromide is gradually evolved (connected to base bath absorber). At the end of the reaction the cuprous bromide was removed by filtration, and the carbon tetrachloride solution was passed through a 35-mm. Chromatographic column filled with 200 g. of alumina. The column is eluted with 200 ml of CH2Cl2. The combined eluates are evaporated to dryness to give 24 g. (87%) of 9-bromoanthracene-d9 as a lemon-yellow solid. It contains impurity of the starting material (~2%) and the dibromo-byproduct (~2%). This material was used directly in further coupling reactions without purification. The intermediate can be further purified to by recrystallization using hexane or cyclohexane to give the pure compound.

Intermediate 4B:

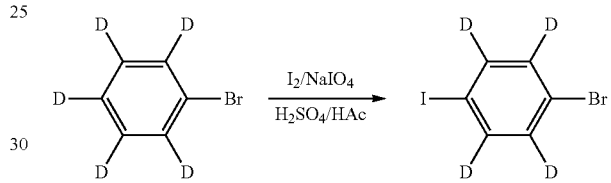

To d5-bromobenzene (MW 162, 100 g, 0.617 mol), was added a mixture solvents of 93 mL of 50% H₂SO₄, and 494 mL of HOAc at rt. Then a pulverized I₂ (MW 254, 61.7 g, 0.243 mol) was added followed by pulverized NaIO₄ (MW 214, 26.4 g, 0.123 mol). The mixture was vigorously stirred and heated to 90° C. for 4 h. The dark purple color solution changed to a pale-orange-colored mixture containing a very fine white precipitate. The mixture was allowed to cool to rt overnight. During this time, the product precipitated as microcrystalline plates. The mixture was filtered and was washed twice 10% sodium thiosulfate Na₂S₂O₃ (50 mL) and then with water. It was dissolved in CH₂Cl₂ and run flash column. The light yellow, crystalline material was obtained 124 g (70%). The filtrate was extracted with CH₂Cl₂ (50 mL×3) and combined the CH₂Cl₂ washed twice 10% sodium thiosulfate Na₂S₂O₃ (50 mL) and then with water. After dried and evaporated the solvent and run flash column to give another 32 g of pure product (17.5%). Total is 156 g (yield 88%).

Intermediate 4C:

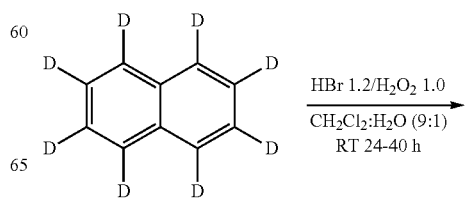

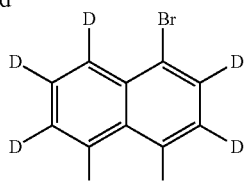

To a stirred solution of naphthalene-d8 (MW 136, 68 g, 0.5 mole) in CH2Cl2 (800 mL): H2O (80 mL) and hydrobromic acid (MW: 81, d=1.49, 100 g; 67.5 mL of a 49% aq. solution; 0.6 mol) was slowly added hydrogen peroxide (FW: 34, d=1.1 g/mL, 56 g; 51.5 mL of a 30% aq. solution; 0.5 mol) over a period of 30 min at 10-15° C. The reaction was left at room temperature for 40 h whilst monitoring its progress by TLC. After the completion of bromination, the solvent was removed under reduced pressure and the crude product was washed twice 10% sodium thiosulfate Na2S2O3 (50 mL) and then with water. The pure product was isolated by flash column chromatography on silica gel (100-200 mesh) using hexane (100%) followed by distillation to give pure 1-bromonaphthene-d7 as a clear liquid 85 g, the yield is around 80%.

Intermediate 4D:

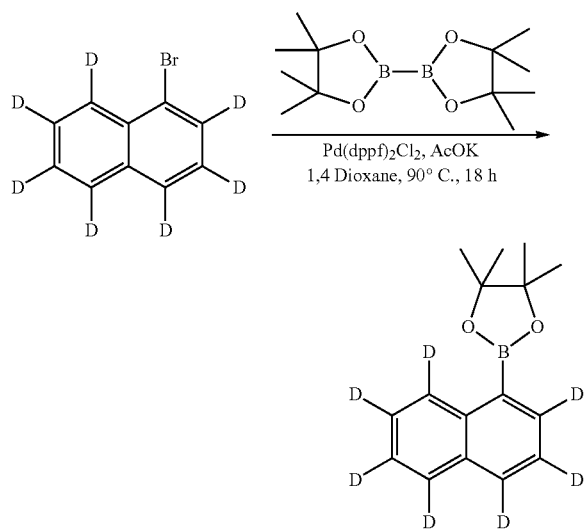

The mixture of 1-bromonaphthalene-d7 (21.4 g, 0.10 mol), bis(pinacolato)diboron (38 g, 0.15 mol), potassium acetate (19.6 g, 0.20 mol) in 300 ml of dry 1,4-dioxane was bubbled with nitrogen for 15 min. Then Pd(dppf)2Cl2—CH2Cl2 (1.63 g, 0.002 mol) was added. The mixture was heated at 100° C. (oil bath) for 18 h. After cooling down the mixture was filtered through Celite and then concentrated to 50 mL, then added water and extracted with ether for three times (100 mL×3). The organic layer was washed with water (3×) and brine (1×), dried over MgSO4, filtered and concentrated. The residue was submitted to a silica gel column (eluent: hexane) to give a white liquid which has by products of naphthalene, and diboronic ester. Thus further purification was conducted by distillation to give a viscous clear liquid. Yield 21 g, 82%.

Intermediate 4E:

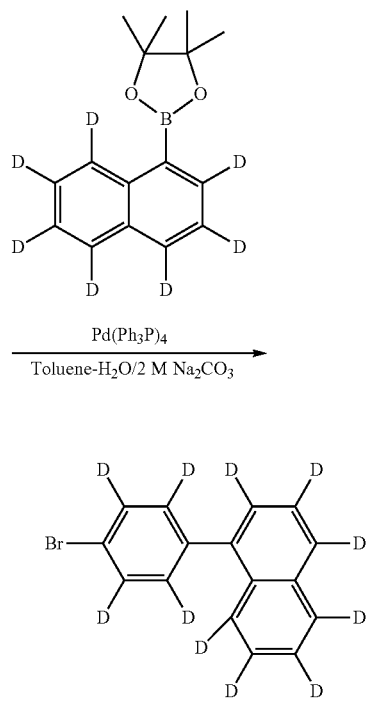

To a mixture of 1-bromo-4-iodo-benzene-D4 (10.95 g, 0.0382 mole) and 1-naphthalene boronic ester-D7 (10.0 g, 0.0383 mole) in Toluene (300 mL) was added Na2CO3 (12.6 g, 0.12 mole) and H2O (50 mL), Aliquat® (3 g). The mixture was bubbled with nitrogen for 15 min. Then Pd(PPh3)4 (0.90 g, 2%) was added. The mixture was refluxed for 12 h under a nitrogen atmosphere. After cooling down the reaction mixture was separated, the organic layer was washed with water and separated, dried and concentrated. Silica was added and concentrated. After evaporation the residue solvent, it was subject to run flash column using hexane as eluent to give crude product. Further purification was conducted by distillation (collect 135-140° C./100 mtorr) to give clear viscous liquid (8.76 g, yield 78%).

Intermediate 4F:

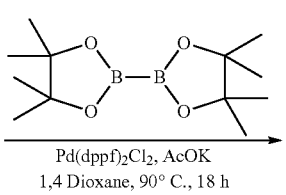

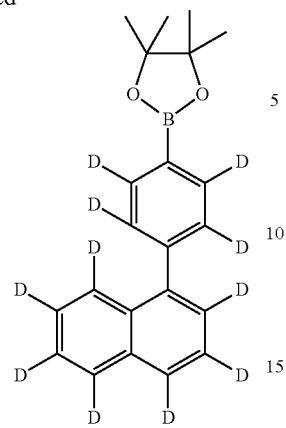

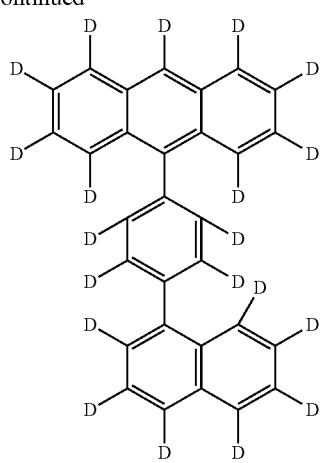

The mixture of 1-bromo-phenyl-4-naphthalene-d11 (22 g, 0.075 mole), bis(pinacolato)diboron (23 g, 0.090 mol), potassium acetate 22 g, 0.224 mol) in 200 ml of dry 1,4-dioxane was bubbled with nitrogen for 15 min. Then Pd(dppf)$_2$Cl$_2$.CH$_2$Cl$_2$ (1.20 g, 0.00147 mol) was added. The mixture was heated at 100° C. (oil bath) for 18 h. After cooling down the mixture was filtered through Celite and then concentrated to 50 mL, then added water and extracted with ether for three times (100 mL×3). The organic layer was washed with water (3×) and brine (1×), dried over MgSO$_4$, filtered and concentrated. The residue was submitted to a silica gel column (eluent: hexane) to give a white liquid which has by products of naphthalene, and diboronic ester. Thus further purification was conducted by run silica gel column again using hexane as eluent. After evaporate the solvent and concentrated to around 80 mL hexane and white crystal product was formed, it was filtrate to give 20.1 g of product, yield 81%.

Intermediate 4G:

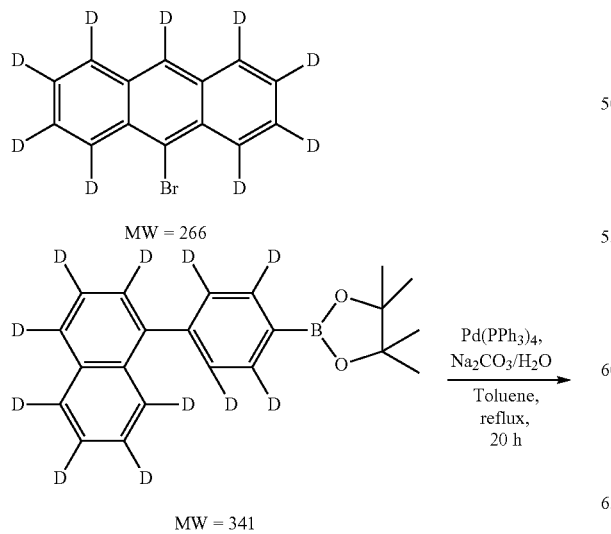

To the intermediate 4A (18.2 g) and intermediate 4F boronic ester (25.5 g) in Toluene (500 mL) was added Na$_2$CO$_3$ (31.8 g) and H$_2$O (120 mL), Aliquat® (5 g). The mixture was bubbled with nitrogen for 15 min. Then Pd(PPh3)4 (1.5 g, 1.3%) was added. The mixture was refluxed for 12 h under a nitrogen atmosphere. After cooling down the reaction mixture was separated, the organic layer was washed with water and separated, dried and concentrated to ~50 mL and poured into MeOH. The solid was filtered to give a yellow crude product (~28.0 g). The crude product was washed with water, HCl (10%), water and methanol. It was redissolved in CHCl$_3$, dried over MgSO4, filtered. The filtrate was added silica gel, concentrated and dried, purified on silica gel (0.5 Kg) using hexane only as eluent (total of 50 L hexane passed—recycled using only 5 L of hexane) to give the white product.

Intermediate 4H:

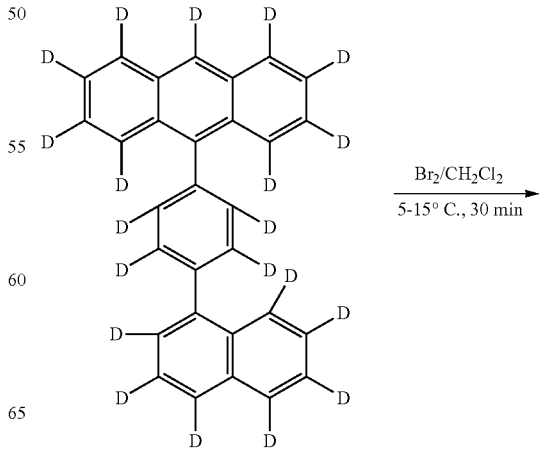

49

-continued

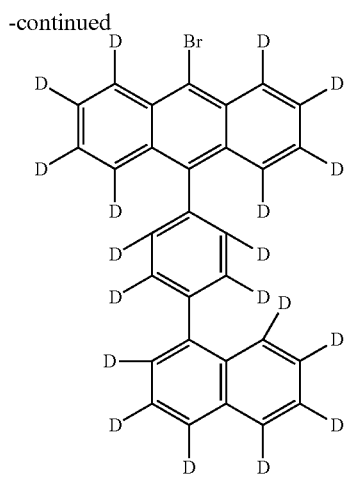

Into a ice-bath cooled solution of 9-(4-naphthalen-1-yl) phenylanthracene-D20, Intermediate 4G, (MW 400.6, 20.3 g, 0.05 mole) in CH2Cl2 (450 mL) was added slowly (20 min) of bromine (MW 160, 8.0 g, 0.05 mole) dissolved in CH2Cl2 (150 mL). The reaction immediately occurred and the color changed to light yellow. Add a solution of Na2S2O3 (2M 100 mL) and stirred for 15 min. Then separated the water layer and the organic phase was washed by Na2CO3 (10%, 50 mL), followed by three times of water. Separated and then dried by MgSO4 and after evaporated the solvent till 100 mL left. Powered into methanol (200 mL) and filtered to give 23.3 g of pure compound (MW 478.5, yield 97.5%) HPLC shows 100% purity.

Intermediate 4I:

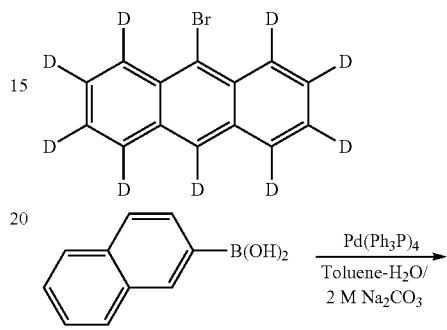

The mixture of naphthalene-D8 (13.6 g, 0.10 mole), bis (pinacolato)diboron (27.93 g, 0.11 mole), di-mu-methoxobis (1,5-cyclooctadiene)diiradium (I) [Ir(OMe)COD]₂ (1.35 g, 2 mmole, 2%) and 4,4'-di-tert-butyl-2,2'-bipyridine (1.1 g, 4 mmole) was added to cyclohexane (200 mL). The mixture was degassed with N2 for 15 min, then heated at 85° C. (oil bath) overnight (dark brown solution). The mixture was passed through a pad of silica gel. The fractions were collected and concentrated until dry. Hexane was added. The filtrate was concentrated (liquid) and passed through a silica gel column, rinsing with hexane to give clear liquid, it was not pure and was purified again by silica gel column, rinsing with hexane followed by distillation at 135° C./100 mmtorr to give pure white viscous liquid and it solidified to give a white powder (18.5 g. Yield 70%).

Intermediate 4J:

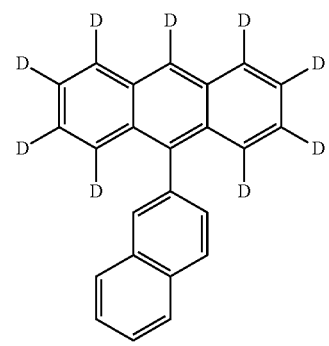

Into a round-bottom flask (100 mL) was added 9-bromoanthracene-d9 (MW 266, 2.66 g, 0.01 mole), naphthelen-2-boronic acid (MW 172, 1.72 g, 0.01 mol), followed by the addition of toluene (30 mL), The mixture was purged with N2 for 10 min. Then Na₂CO₃ (2M, 10 mL (2.12 g) 0.02 mole) dissolved in the water (10 mL) was added. The mixture was continued to purge with N₂ for 10 min. A catalyst amount of Pd(PPh₃)₄ (0.25 g, 2.5%, 0.025 mmol) was added. The mixture was refluxed overnight. Separated the organic layer then poured into menthol, washed with water, HCl (10%), water and methanol. It gives 2.6 g pure white product. (Yield: 83%).

Intermediate 4K:

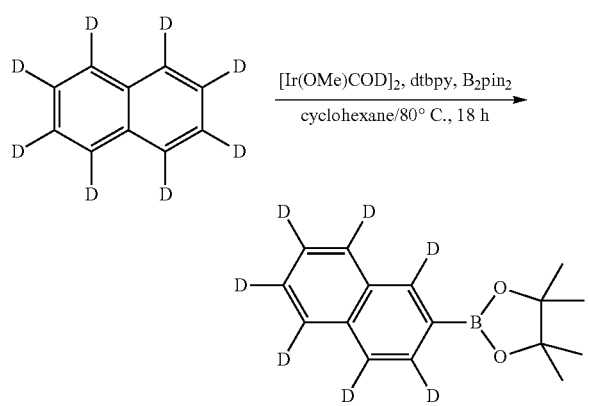

-continued

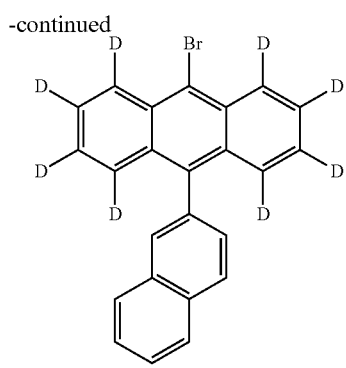

A solution of (2.6 g 0.0083 mole) 9-2'-naphthyl-anthracene-d9, intermediate 4J in CH2Cl2 (50 mL) was added dropwise a solution of bromine (1.33 g, 0.0083 mole) in CH2Cl2 (5 mL) and stirred for 30 min. Add a solution of Na2S2O3 (2M 10 mL) and stirred for 15 min. Then separated the water layer and the organic phase was washed by Na2CO3 (10%, 10 mL), followed by three times of water. Separated and then dried by MgSO4 and after evaporated the solvent till 20 mL left. Powered into methanol (100 mL) and filtered give pure compound (3.1 g, yield 96%).

Intermediate 4L:

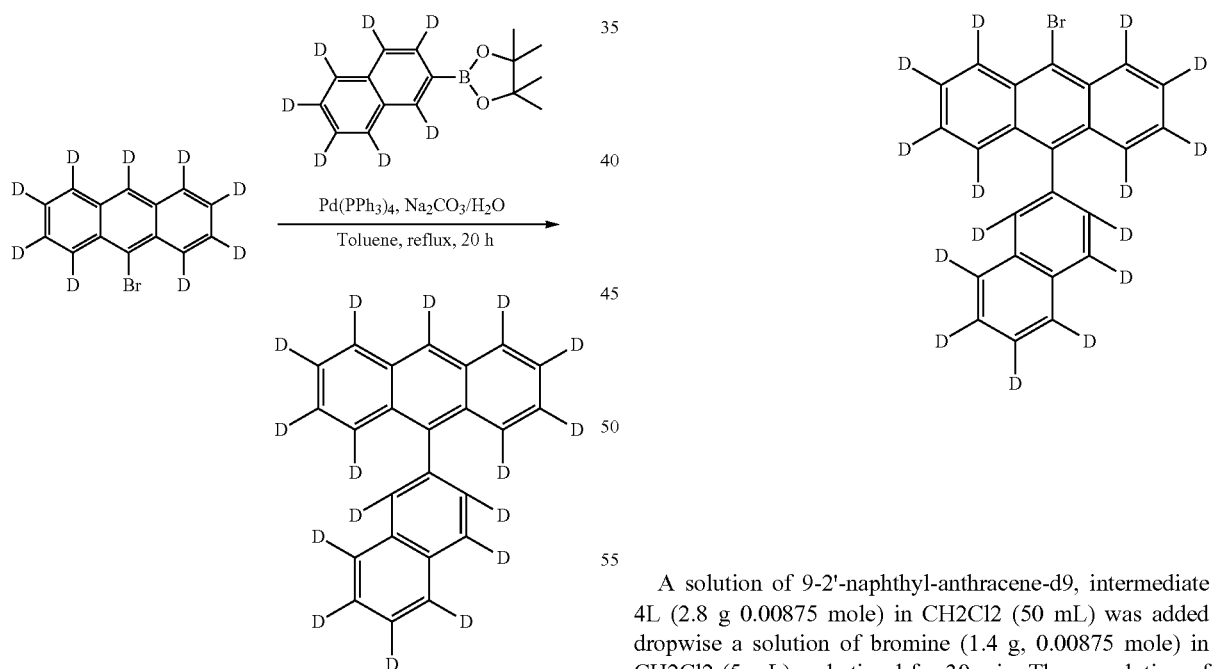

To a mixture of 9-bromoanthracene-D9, intermediate 4K (2.66 g, 0.01 mole) and 4,4,5,5-tetramethyl-2-(naphthalene-2-yl-D7)-1,3,2-dioxaborolane (2.7 g, 0.011 mole) in Toluene (~60 mL) was added Na₂CO₃ (4.0 g, 0.04 mole) and H2O (20 mL). The mixture was bubbled with nitrogen for 15 min. Then Pd(PPh₃)₄ (0.20 g, 2.0%) was added. The mixture was refluxed for 18 h under a nitrogen atmosphere (yellow solids). After cooling down the reaction mixture, it was poured into MeOH (200 mL). The solid was filtered to give a yellow crude product. The crude product was washed with water, and methanol. It was redissolved in CHCl₃, dried over MgSO4, filtered. The filtrate was added silica gel, concentrated and dried, purified on silica gel using hexane as eluent to give the pure product (3.0 g, yield 94%).

Intermediate 4M:

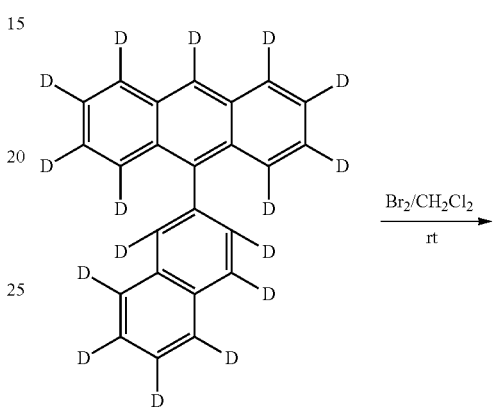

A solution of 9-2'-naphthyl-anthracene-d9, intermediate 4L (2.8 g 0.00875 mole) in CH2Cl2 (50 mL) was added dropwise a solution of bromine (1.4 g, 0.00875 mole) in CH2Cl2 (5 mL) and stirred for 30 min. Then a solution of Na2S2O3 (2M 10 mL) was added and the mixture was stirred for 15 min. Then separated the water layer and the organic phase was washed by Na2CO3 (10%, 10 mL), followed by three times of water. Separated and then dried by MgSO4 and after evaporated the solvent till 20 mL left. Powered into methanol (100 mL) and filtered give pure compound (3.3 g, yield 95%).

Example 5

This example illustrates the synthesis of Compound H8 from Intermediate 4H and Intermediate 4I.

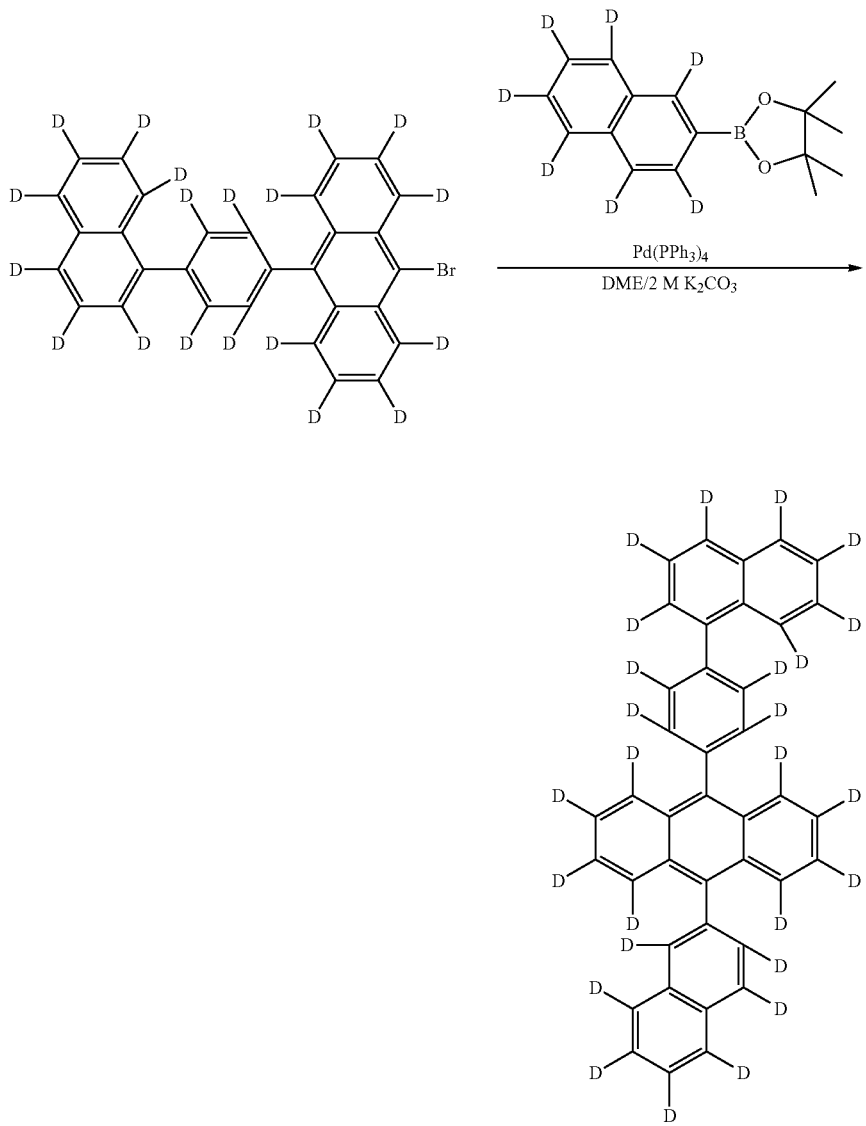

To a mixture of 9bromo-10-(4-naphthalen-1-yl)phenylanthracene-D19 intermediate 4H (14.84 g, 0.031 mole) and 2-naphthalen boronic ester intermediate 4I (10.0 g, 0.038 mole) in DME (350 mL) was added $K_2CO_3$ (12.8 g, 0.093 mole) and H2O (40 mL). The mixture was bubbled with nitrogen for 15 min. Then Pd(PPh3)4 (0.45 g, 1.3%) was added. The mixture was refluxed for 12 h under a nitrogen atmosphere. After cooling down the reaction mixture was concentrated to ~150 mL and poured into MeOH. The solid was filtered to give a light yellow crude product. The crude product was washed with water, and methanol. It was redissolved in $CHCl_3$, dried over MgSO4, filtered. The filtrate was added silica gel, concentrated and dried, purified on silica gel (0.5 Kg) using hexane:chloroform (3:1) as eluent to give the white product. (15 g, yield 91%)

Example 6

This example illustrates the synthesis of Compound H11 from Intermediate 4K.

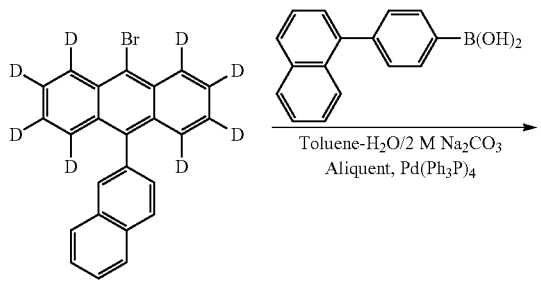

Into a round-bottom flask (100 mL) was added 9-bromo-10-(naphthalene-2-yl)anthracene, intermediate 4K (1.96 g, 0.05 mol), 4-(naphthalene-1-yl)phenylboronic acid (1.49 g, 0.06 mol), followed by the addition of toluene (30 mL). The mixture was purged with N2 for 10 min. Then $Na_2CO_3$ (1.90 g, 0.018 mole) dissolved in the water (8 mL) was added, followed by Aliquat® (1 mL). The mixture was continued to purge with N2 for 10 min. A catalyst amount of Pd(PPh3)4 (116 mg) was added. The mixture was refluxed overnight. After split of aqueous phase, organic layer was poured into methanol (100 mL) to collect the white solid. It was filtrated and further purification was conducted by running the silica gel column using chloroform:hexane (1:3) to give pure white compound (2.30 g, yield 90%).

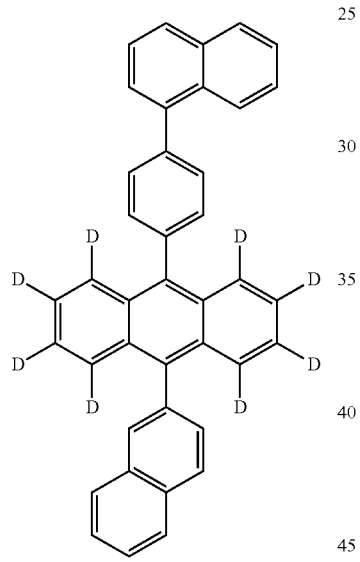

Example 7

This example illustrates the synthesis of Compound H9 from Intermediate 4K and Intermediate 4F.

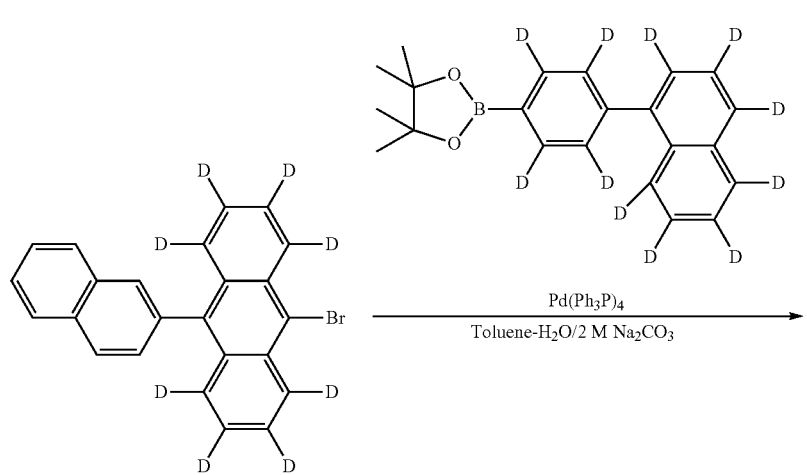

-continued

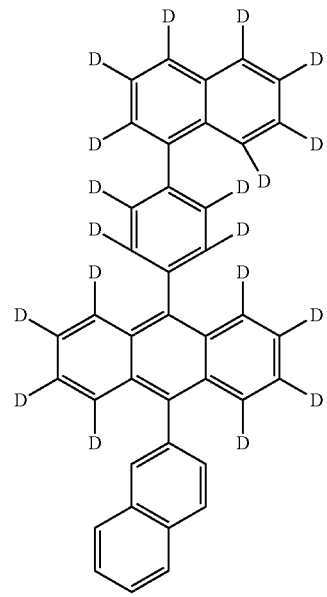

Into a round-bottom flask (100 mL) was added 9-bromo-10-(naphthalene-2-yl)anthracene-D8, intermediate 4K (0.70 g, 0.0018 mol), 4-(naphthalene-1-yl)phenylboronic acid-D11, intermediate 4F (0.7 g, 0.002 mol), followed by the addition of toluene (10 mL). The mixture was purged with N2 for 10 min. Then $Na_2CO_3$ (0.64 g, 0.006 mole) dissolved in the water (3 mL) was added, followed by Aliquat® 0.1 mL). The mixture was continued to purge with N2 for 10 min. A catalyst amount of Pd(PPh3)4 (0.10 g) was added. The mixture was refluxed overnight. After split of aqueous phase, organic layer was poured into methanol (100 mL) to collect the white solid. It was filtrated and further purification was conducted by running the silica gel column using chloroform:hexane (1:3) to give pure white compound (0.90 g, yield 95%).

Compounds H10, H12 and H13 were prepared in an analogous manner.

Examples 8-10 and Comparative Examples D and E

These examples demonstrate the fabrication and performance of a device with a blue emitter.

The device had the following structure on a glass substrate:
anode=ITO (50 nm)
hole injection layer=HIJ1 (50 nm).
hole transport layer=polymer P1 (20 nm)
electroactive layer=13:1 host:dopant (40 nm), as shown in Table 3
electron transport layer=ET1 (10 nm)
cathode=CsF/Al (1.0/100 nm)

TABLE 3

| Device Electroactive Layers | | |
|---|---|---|
| Example | Host | D13 |
| Comparative D-1 | Comp. Compound A | D13 |
| Comparative D-2 | Comp. Compound A | D13 |
| Ex. 8-1 | H11 | D13 |
| Ex. 8-2 | H11 | D13 |
| Ex. 9-1 | H8 | D13 |

TABLE 3-continued

| Device Electroactive Layers | | |
|---|---|---|
| Example | Host | D13 |
| Ex. 9-2 | H8 | D13 |
| Comparative E-1 | Comp. Compound A | D13 |
| Comparative E-2 | Comp. Compound A | D13 |
| Ex. 10-1 | H10 | D13 |
| Ex. 10-2 | H10 | D13 |

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ1 was spin-coated over the ITO surface and heated to remove solvent. After cooling, the substrates were then spin-coated with a solution of a hole transport material, and then heated to remove solvent. After cooling the substrates were spin-coated with the emissive layer solution, and heated to remove solvent. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current needed to run the device. The unit is a cd/A. The power efficiency is the current efficiency multiplied by pi, divided by the operating voltage. The unit is lm/W. The device data is given in Table 4.

TABLE 4

Device Performance

| Ex. | CIE (x, y) | Voltage (V) | C.E. (cd/A) | E.Q.E. (%) | P.E. (lm/W) | Lifetest current density (mA/cm2) | Lifetest Luminance (nits) | Raw T50 (h) | Projected Lifetime T50 @1000 nits |
|---|---|---|---|---|---|---|---|---|---|
| Comp. D-1 | 0.136, 0.126 | 4.4 | 5.7 | 5.5 | 4.1 | 127 | 6686 | 455 | 11503 |
| Comp. D-2 | 0.136, 0.123 | 4.4 | 5.8 | 5.7 | 4.2 | 129 | 6572 | 450 | 11048 |
| Ex. 8-1 | 0.136, 0.121 | 4.4 | 5.8 | 5.8 | 4.2 | 128 | 6669 | 555 | 13970 |
| Ex. 8-2 | 0.136, 0.124 | 4.3 | 5.9 | 5.7 | 4.2 | 130 | 6599 | 590 | 14587 |
| Ex. 9-1 | 0.136, 0.121 | 4.3 | 5.8 | 5.8 | 4.2 | 127 | 6475 | 940 | 22503 |
| Ex. 9-2 | 0.136, 0.121 | 4.4 | 5.8 | 5.8 | 4.2 | 124 | 6254 | 955 | 21551 |
| Comp. E-1 | 0.136, 0.123 | 4.4 | 6.1 | 6.0 | 4.3 | 124 | 6670 | 400 | 10071 |
| Comp. E-2 | 0.135, 0.124 | 4.4 | 5.8 | 5.6 | 4.1 | 131 | 7006 | 388 | 10620 |
| Ex. 10-1 | 0.136, 0.121 | 4.4 | 6.0 | 5.9 | 4.2 | 123 | 6403 | 622 | 14610 |
| Ex. 10-2 | 0.136, 0.118 | 4.4 | 5.7 | 5.8 | 4.1 | 121 | 6050 | 675 | 14398 |

* All data @ 1000 nits,
CE = current efficiency;
CIEx and CIEy are the x and y color coordinates according to the C.I.E. chromaticity scale (Commission Internationale de L'Eclairage, 1931).
Raw T50 is the time in hours for a device to reach one-half the initial luminance at the lifetest luminance given.
Projected T50 is the projected lifetime at 1000 nits using an accelerator factor of 1.7.

It can be seen that with the deuterated hosts of the invention, the lifetime of devices is greatly increased, while maintaining other device properties. The average projected lifetimes for different hosts are given in Table 5, below.

TABLE 5

Device lifetimes

| Host | Average Projected Lifetime T50 @ 1000 nits, in hours |
|---|---|
| Comparative Compound A | 11,276 and 10,346 |
| H8 | 22,027 |
| H10 | 14,504 |
| H11 | 14,279 |

Example 11 and Comparative Example F

This example demonstrates the fabrication and performance of a device having an electroactive layer with a green dopant, a first host having Formula I, and a second host material. The electron transport material was ET2, shown below.

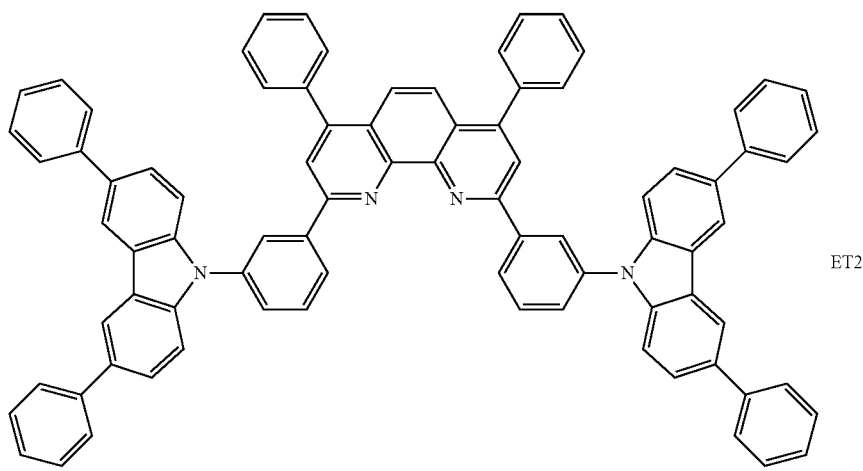 [SMILES: c1ccc(-c2ccc3c(c2)c2cc(-c4ccccc4)ccc2n3-c2cccc(-c3cc(-c4ccccc4)c4ccc5c(-c6ccccc6)cc(-c6cccc(-n7c8ccc(-c9ccccc9)cc8c8cc(-c9ccccc9)ccc87)c6)nc5c4n3)c2)cc1]

ET2

The device had the following structure on a glass substrate:
anode=ITO (50 nm)
hole injection layer=HIJ2, (50 nm), which is an aqueous dispersion of an electrically conductive polymer and a polymeric fluorinated sulfonic acid. Such materials have been described in, for example, published U.S. patent applications US 2004/0102577, US 2004/0127637, US 2005/0205860, and published PCT application WO 2009/018009.
hole transport layer=polymer P1 (20 nm)
electroactive layer=82.5:5:12.5 first host:second host: dopant (60 nm), as shown in Table 6
electron transport layer=ET2 (10 nm).
cathode=CsF/Al (0.7/100 nm)

TABLE 6

Device Electroactive Layers

| Example | First Host | Second Host | Dopant |
|---|---|---|---|
| Comparative F | Comparative Compound A | D12 | D6 |
| Ex. 11 | H8 | D12 | D6 |

Devices were made and evaluated as described for Examples 8-10. The device data is given in Table 7.

TABLE 7

Device Performance

| Ex. | CIE (x, y) | Voltage (V) | C.E. (cd/A) | E.Q.E. (%) | P.E. (lm/W) | Lifetest current density (mA/cm2) | Lifetest Luminance (nits) | Raw T50 (h) | Projected Lifetime T50 @1000 nits |
|---|---|---|---|---|---|---|---|---|---|
| Comp. F | 0.265, 0.649 | 4.8 | 26.1 | 7.2 | 17.1 | 134 | 29167 | 1800 | 557,000 |
| Ex. 11 | 0.257, 0.650 | 4.7 | 25.4 | 7.1 | 16.9 | 127 | 27232 | 4160 | 1,144,800 |

* All data @ 1000 nits,
CE = current efficiency;
CIEx and CIEy are the x and y color coordinates according to the C.I.E. chromaticity scale (Commission Internationale de L'Eclairage, 1931).
Raw T50 is the time in hours for a device to reach one-half the initial luminance at the lifetest luminance given.
Projected T50 is the projected lifetime at 1000 nits using an accelerator factor of 1.7.

It can be seen that with the deuterated host of the invention, the lifetime of the device is greatly increased, while maintaining other device properties. The projected lifetime more than doubles, even with the presence of a non-deuterated second host material.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An aryl-substituted anthracene compound having Formula I:

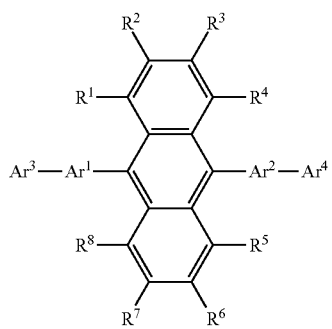

Formula I wherein:
  $R^1$ through $R^8$ are the same or different at each occurrence and are selected from the group consisting of H, D, alkyl, alkoxy, aryl, aryloxy, siloxane, and silyl;
  $Ar^1$ and $Ar^2$ are the same or different and are selected from the group consisting of aryl groups; and
  $Ar^3$ and $Ar^4$ are the same or different and are selected from the group consisting of H, D, and aryl groups;
  wherein the compound has at least one D.

2. The compound of claim 1, which is at least 10% deuterated.

3. The compound of claim 1, which is at least 50% deuterated.

4. The compound of claim 1, which is 100% deuterated.

5. The compound of claim 1, wherein the at least one D is on a substituent group on an aryl ring.

6. The compound of claim 1, wherein at least one of $R^1$ through $R^8$ is D.

7. The compound of claim 1, wherein $R^1$ through $R^8$ are selected from H and D.

8. The compound of claim 1, wherein at least one of $R^1$ through $R^8$ is selected from alkyl, alkoxy, aryl, aryloxy, siloxane, and silyl, and the remainder of $R^1$ through $R^8$ are selected from H and D.

9. The compound of claim 8, wherein $R^2$ is selected from alkyl and aryl.

10. The compound of claim 1, wherein at least one of $Ar^1$ through $Ar^4$ is a deuterated aryl.

11. The compound of claim 1, wherein $Ar^3$ and $Ar^4$ are selected from D and deuterated aryls.

12. The compound of claim 1, wherein $Ar^1$ through $Ar^4$ are at least 20% deuterated.

13. The compound of claim 1, wherein $Ar^1$ and $Ar^2$ are selected from the group consisting of phenyl, naphthyl, phenanthryl, anthracenyl, and deuterated derivatives thereof.

14. The compound of claim 5, wherein $Ar^3$ and $Ar^4$ are selected from the group consisting of phenyl, naphthyl, phenanthryl, anthracenyl, phenylnaphthylene, naphthylphenylene, deuterated derivatives thereof and a group having Formula II:

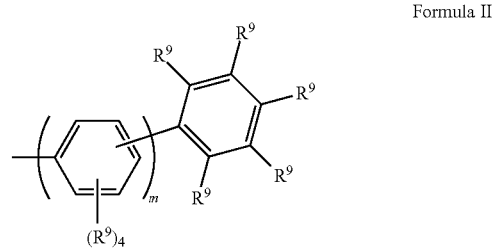

Formula II where:
  $R^9$ is the same or different at each occurrence and is selected from the group consisting of H, D, alkyl, alkoxy, siloxane and silyl, or adjacent $R^9$ groups may be joined together to form an aromatic ring; and
  m is the same or different at each occurrence and is an integer from 1 to 6.

15. The compound of claim 1, wherein $Ar^3$ and $Ar^4$ are selected from the group consisting of phenyl, naphthyl, phenylnaphthylene, naphthylphenylene, deuterated derivatives thereof, and a group having Formula III:

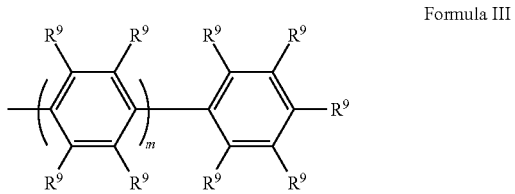

Formula III where:
  $R^9$ is the same or different at each occurrence and is selected from the group consisting of H, D, alkyl, alkoxy, siloxane and silyl, or adjacent $R^9$ groups may be joined together to form an aromatic ring; and
  m is the same or different at each occurrence and is an integer from 1 to 6.

16. The compound of claim 1, wherein at least one of $Ar^1$ through $Ar^4$ is a heteroaryl group.

17. The compound of claim 16, wherein the heteroaryl group is selected from carbazole, benzofuran, and dibenzofuran.

18. The compound of claim 1, wherein at least one of $R^1$ through $R^8$ is D and at least one of $Ar^1$ through $Ar^4$ is a deuterated aryl.

19. An organic electronic device comprising a first electrical contact layer, a second electrical contact layer, and at least one active layer therebetween, wherein the active layer comprises an aryl-substituted anthracene compound having Formula I:

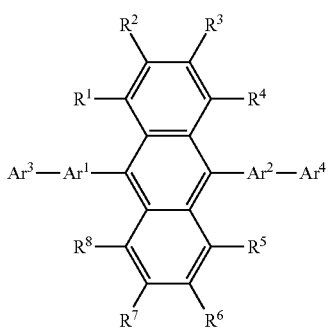

Formula I wherein:
- $R^1$ through $R^8$ are the same or different at each occurrence and are selected from the group consisting of H, D, alkyl, alkoxy, aryl, aryloxy, siloxane, and silyl;
- $Ar^1$ and $Ar^2$ are the same or different and are selected from the group consisting of aryl groups; and
- $Ar^3$ and $Ar^4$ are the same or different and are selected from the group consisting of H, D, and aryl groups;
- wherein the compound has at least one D.

20. The device of claim 19, wherein the active layer is an electroactive layer which further comprises an electroactive dopant compound.

21. The device of claim 19, wherein the active layer is an electroactive layer and consists essentially of a compound having Formula I and an electroactive dopant compound.

22. The device of claim 19, wherein the active layer is an electroactive layer and consists essentially of a compound having Formula I, a second host material, and an electroactive dopant compound.

23. The device of claim 20, wherein the electroluminescent compound is selected from the group consisting of amino-substituted chrysenes and amino-substituted anthracenes.

24. The device of claim 22, further comprising a hole injection layer between the first electrical contact layer and the active layer.

25. The device of claim 24, wherein the hole injection layer comprises at least one electrically conductive polymer and at least one fluorinated acid polymer.

26. An aryl-substituted anthracene compound having Formula I:

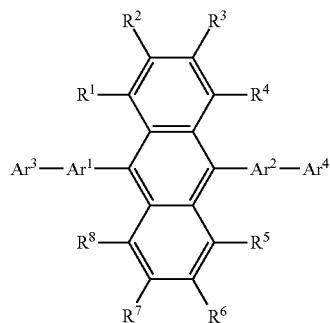

Formula I wherein:
- $R^1$ through $R^8$ are the same or different at each occurrence and are selected from the group consisting of H and D;
- $Ar^1$ and $Ar^2$ are the same or different and are selected from the group consisting of aryl groups; and
- $Ar^3$ and $Ar^4$ are the same or different and are selected from the group consisting of H, D, and aryl groups;
- wherein the compound has at least one D.

27. An organic electronic device comprising a first electrical contact layer, a second electrical contact layer, and at least one active layer therebetween, wherein the active layer comprises an aryl-substituted anthracene compound having Formula I:

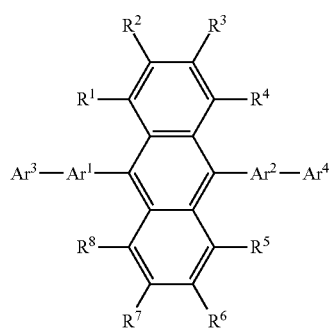

Formula I wherein:
- $R^1$ through $R^8$ are the same or different at each occurrence and are selected from the group consisting of H and D;
- $Ar^1$ and $Ar^2$ are the same or different and are selected from the group consisting of aryl groups; and
- $Ar^3$ and $Ar^4$ are the same or different and are selected from the group consisting of H, D, and aryl groups;
- wherein the compound has at least one D.

28. The aryl-substituted anthracene compound of claim 1 wherein $R^1$ through $R^8$ are the same or different at each occurrence and are selected from the group consisting of H, D, alkyl, alkoxy, aryl, and aryloxy and which is at least 10% deuterated.

* * * * *